(12) United States Patent
Fridman et al.

(10) Patent No.: US 12,068,058 B2
(45) Date of Patent: Aug. 20, 2024

(54) CUT VERTEX METHOD FOR IDENTIFYING COMPLEX MOLECULE SUBSTRUCTURES

(71) Applicant: Merck Sharp & Dohme LLC, Rahway, NJ (US)

(72) Inventors: Arthur Fridman, Brooklyn, NY (US); Ansuman Bagchi, Plaisboro, NY (US); Xiang Yu, North Wales, PA (US); Mark Cancilla, Philadelphia, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 901 days.

(21) Appl. No.: 16/973,197

(22) PCT Filed: Jun. 11, 2019

(86) PCT No.: PCT/US2019/036467
§ 371 (c)(1),
(2) Date: Dec. 8, 2020

(87) PCT Pub. No.: WO2019/241191
PCT Pub. Date: Dec. 19, 2019

(65) Prior Publication Data
US 2021/0257046 A1    Aug. 19, 2021

Related U.S. Application Data

(60) Provisional application No. 62/770,252, filed on Nov. 21, 2018, provisional application No. 62/752,152, (Continued)

(51) Int. Cl.
*G16B 15/00* (2019.01)
*G06F 16/22* (2019.01)
(Continued)

(52) U.S. Cl.
CPC ......... *G16B 15/00* (2019.02); *G06F 16/2455* (2019.01); *G06F 16/9024* (2019.01);
(Continued)

(58) Field of Classification Search
CPC ............. G06F 16/2455; G06F 16/9024; G06F 16/248; G06F 16/9535; G06F 16/22;
(Continued)

(56) References Cited

U.S. PATENT DOCUMENTS 9,700,359 B2    7/2017    Hatch et al.
10,392,443 B2   8/2019    Chakraborty et al.
(Continued)

FOREIGN PATENT DOCUMENTS

CN    104765984 A    7/2015
CN    107077592 A    8/2017
(Continued)

OTHER PUBLICATIONS

Ezan et al., "Assessment of the metabolism of therapeutic proteins and antibodies," Expert Opinion on Drug Metabolism & Toxicology, vol. 10, No. 8, pp. 1079-0191, 2014.
(Continued)

*Primary Examiner* — Manish S Shah
*Assistant Examiner* — Christian T Bryant
(74) *Attorney, Agent, or Firm* — Grady L. White; Potomac Law Group, PLLC

(57) ABSTRACT

Embodiments of the present invention avoid the processing problems associated with using conventional computer systems for identifying and characterizing all of the substructures (e.g., metabolites) of large complex molecules by using a defined minimum cleavable unit (MCU) and an MCU graph for a chosen molecule, as well as a "cut vertex" in the MCU graph for the chosen molecule. The system splits the MCU graph of the chosen molecule at the specified cut
(Continued)

OVERALL DATA FLOW DIAGRAM vertex to produce two separate MCU graph components (i.e., a first MCU subgraph and a second MCU subgraph) of the chosen molecule, and generates and traverses a first line graph component and a second line graph component, respectively, for the two MCU subgraph components with a graph traversing algorithm to generate and store in memory a first database of substructures and molecular weights for the first component, and a second database of substructures and molecular weights for the second line graph component. Subsequently, embodiments of the present invention can perform binary searches on the two databases (or the two subsections of a single database) to identify and produce graphic representations of all of the substructures of the chosen molecule that have molecular weights that match the query molecular weight (or range of query molecular weights), including the substructures of the chosen molecule that straddle (i.e., include) the cut vertex.

30 Claims, 29 Drawing Sheets

Related U.S. Application Data filed on Oct. 29, 2018, provisional application No. 62/683,582, filed on Jun. 11, 2018.

(51) Int. Cl.
  *G06F 16/2455* (2019.01)
  *G06F 16/248* (2019.01)
  *G06F 16/901* (2019.01)
  *G06F 16/9535* (2019.01)
  *G16B 45/00* (2019.01)
  *G16B 50/00* (2019.01)
  *G16C 20/20* (2019.01)
  *G16C 20/40* (2019.01)
  *G16C 20/80* (2019.01)
  *G16C 20/90* (2019.01)

(52) U.S. Cl.
  CPC ............ *G16C 20/20* (2019.02); *G16C 20/40* (2019.02); *G16C 20/80* (2019.02); *G16C 20/90* (2019.02); *G06F 16/22* (2019.01); *G06F 16/248* (2019.01); *G06F 16/9535* (2019.01); *G16B 45/00* (2019.02); *G16B 50/00* (2019.02)

(58) Field of Classification Search
  CPC ........ G16C 20/20; G16C 20/40; G16C 20/80; G16C 20/90; G16B 45/00; G16B 50/00; G16B 15/00; G06B 15/00
  See application file for complete search history.

(56) References Cited

U.S. PATENT DOCUMENTS

| 10,620,217 | B2 | 4/2020 | Bieniarz et al. | |
| 11,854,664 | B2 * | 12/2023 | Fridman | G16C 20/90 |
| 2005/0228592 | A1 | 10/2005 | Ahuja et al. | |
| 2006/0085142 | A1 | 4/2006 | Mistrik | |
| 2007/0213297 | A1 | 9/2007 | Wong | |
| 2008/0120041 | A1 | 5/2008 | Ridder et al. | |
| 2013/0325354 | A1 | 12/2013 | Siegel | |
| 2013/0337456 | A1 | 12/2013 | Honisch et al. | |
| 2014/0045273 | A1 | 2/2014 | Cerda et al. | |
| 2016/0153060 | A1 | 6/2016 | Ling et al. | |
| 2018/0011899 | A1 | 1/2018 | Dean et al. | |
| 2018/0318388 | A1 | 11/2018 | Pandurangi | |

FOREIGN PATENT DOCUMENTS

| CN | 107923888 | A | 4/2018 |
| CN | 107111617 | A | 6/2021 |
| JP | 2007508637 | A | 4/2007 |
| JP | 2007312776 | A | 12/2007 |
| KR | 20070045141 | A | 5/2007 |
| KR | 20140145753 | A | 12/2014 |
| KR | 1020140145753 | A | 12/2014 |
| WO | 0221139 | A2 | 3/2002 |
| WO | 2017131911 | A1 | 8/2017 |

OTHER PUBLICATIONS

Yu et al., "Metabolite Identification of Therapeutic Peptides and Proteins by Top-down Differential Mass Spectrometry and Metabolite Database Matching," Analytical Chemistry, vol. 92, pp. 8298-8305, 2020.

Adai et al., "Creating a Map of Protein Function with an Algorithm for Visualizing Very Large Biological Networks," J. Mol. Biol., vol. 340, pp. 179-190, Jun. 2004.

Bader et al., "An automated method for finding molecular complexes in large protein interaction networks," BMC Bioinformatics, vol. 4, p. 2, Jan. 2003.

Engler et al., "Enumerating common molecular substructures," PeerJ Preprints, pp. 1-10, Sep. 2017.

Fontaine et al., "Results Towards a m/z unlimited algorithm for peptide and protein structure elucidation," 65th ASMS Conference on Mass Spectrometry and Allied Topics, Jun. 2017.

Plomley et al., "The Application of Research Grade MetabolitePilot Softward for the Determination of Exenatide Catabolites using HRAM with SWATH Acquistion," 65th ASMS Conference on Mass Spectrometry and Allied Topics, Jun. 2017.

Radchenko et al., "Software-aided approach to investigate peptide structure and metabolic susceptibility of amide bonds in peptide drugs based on high resolution mass spectrometry," PLoS One, vol. 12, No. 11, e0186461, Nov. 2017.

Siegel et al., "Disulfide Linked Linear Peptides ANP, Insulin, ShK Toxin: Automatic Assignment of Exact-Mass ESI-MS/MS Fragment Ion Structures Using the MASSPEC Algorithm," 64th ASMA Conference on Mass Spectrometry and Allied Topics, Jun. 2016.

Siegel et al., "MASSPEC: a graphics-based data system for correlating a mass spectrum with a proposed structure," Analytica Chimica Acta., vol. 237, pp. 459-472, 1990.

Siegel et al., "MASSPEC: A Powerful Computer Program for Correlating/Elucidating Molecular Structures Using Tandem Mass Spectral Data," 64th Annual ASMS Conference, 2016.

Trexler et al., "Utilization of Mass-MetaSite for in vitro and in vivo Metabolite Identification of Complex Therapeutic Peptides," American Society for Mass Spectrometry, St. Louis, Missouri, US, Jun. 1, 2015.

Wu et al., "Recognizing Protein Substructure Similarity Using Segmental Threading," Structure, vol. 18, No. 7, pp. 858-867, Jul. 2010.

Yu et al., "Unambiguous Metabolite Identification of Peptide and Protein Therapeutics by Top-Down Protein/Peptide MetID Platform," The Delaware Valley Drug Metabolism Discussion Group, Sep. 2016.

Yu et al., "Understanding the Metabolism of Peptide and Protein Therapeutics by Developing a Top-Down Metabolite Identification Program," 64th ASMS Conference on Mass Spectrometry and Allied Topics, Jun. 2016.

Yu et al., "Understanding the Metabolism of Protein and Peptide Therapeutics by Developing a Top Down Protein Metabolite Identification Platform," 2016 APA Conference Abstract, Jun. 2016.

Yu et al., "Understanding the Metabolism of Protein and Peptide Therapeutics by Developing a Top-Down Protein Metabolite Identification Platform," 2016 ASMS Conference Abstract, Jun. 2016.

Yu et al., "Understanding the Metabolism of Protein and Peptide Therapeutics by Developing a Top-Down Protein Metabolite Identification Platform," 12th Annual APA Meeting, Sep. 2016.

(56) References Cited

OTHER PUBLICATIONS

Zhang et al., "HELM: A Hierarchical Notation Language for Complex Biomolecule Structure Representation," Journal of Chemical Information and Modeling, vol. 52, pp. 2796-2806, Sep. 2012.

\* cited by examiner

OVERALL DATA FLOW DIAGRAM

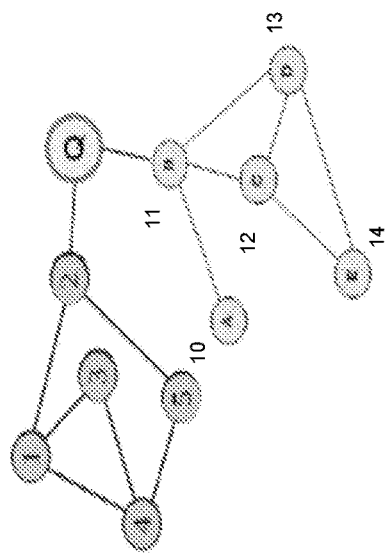
FIG. 9B
FIG. 9A
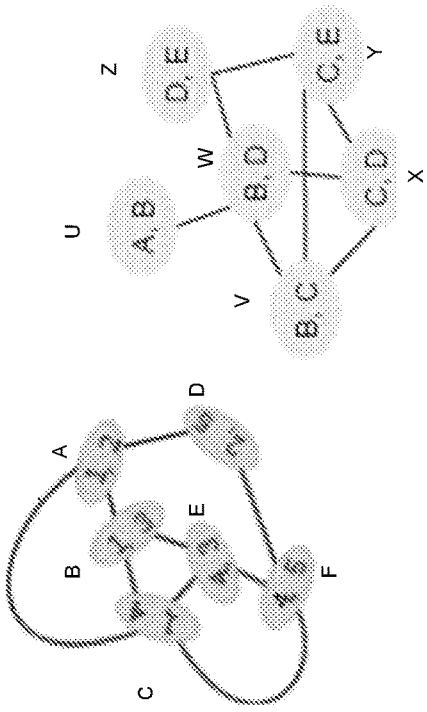
FIG. 9D
FIG. 9C

|   | 1 | 2 | 3 | 4 | 5 | 6 | 7 | 8 | 9 | 10 | 11 | 12 | 13 | 14 |
|---|---|---|---|---|---|---|---|---|---|----|----|----|----|----|
| 1 | 0 | 1 | 0 | 0 | 0 | 0 | 0 | 0 | 0 | 0  | 0  | 1  | 0  | 0  |
| 2 | 1 | 0 | 1 | 0 | 0 | 0 | 0 | 0 | 0 | 0  | 0  | 1  | 0  | 1  |
| 3 | 0 | 1 | 0 | 1 | 0 | 0 | 0 | 0 | 0 | 0  | 0  | 0  | 0  | 1  |
| 4 | 0 | 0 | 1 | 0 | 1 | 0 | 0 | 0 | 0 | 0  | 0  | 0  | 1  | 0  |
| 5 | 0 | 0 | 0 | 1 | 0 | 1 | 0 | 0 | 0 | 0  | 0  | 0  | 1  | 0  |
| 6 | 0 | 0 | 0 | 0 | 1 | 0 | 1 | 0 | 0 | 0  | 0  | 1  | 0  | 0  |
| 7 | 0 | 0 | 0 | 0 | 0 | 1 | 0 | 1 | 0 | 0  | 1  | 0  | 0  | 0  |
| 8 | 0 | 0 | 0 | 0 | 0 | 0 | 1 | 0 | 1 | 0  | 0  | 0  | 0  | 0  |
| 9 | 0 | 0 | 0 | 0 | 0 | 0 | 0 | 1 | 0 | 1  | 0  | 0  | 0  | 0  |
| 10 | 0 | 0 | 0 | 0 | 0 | 0 | 0 | 0 | 1 | 0 | 1  | 0  | 1  | 0  |
| 11 | 0 | 0 | 0 | 0 | 0 | 0 | 1 | 0 | 0 | 1 | 0  | 0  | 1  | 0  |
| 12 | 1 | 1 | 0 | 0 | 0 | 1 | 1 | 0 | 0 | 0 | 0  | 0  | 0  | 0  |
| 13 | 0 | 0 | 0 | 1 | 1 | 0 | 0 | 0 | 0 | 1 | 1  | 0  | 0  | 0  |
| 14 | 0 | 1 | 1 | 0 | 0 | 0 | 0 | 0 | 0 | 0 | 0  | 0  | 0  | 0  |

FIG. 13

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 13 | 0 | 0 | 0 | 0 | 0 | 0 | 0 | 0 | 0 | 0 | 0 | 0 | 0 | 1 |
| 12 | 0 | 0 | 0 | 0 | 0 | 0 | 0 | 0 | 0 | 1 | 0 | 0 | 0 | 0 |
| 11 | 0 | 0 | 0 | 0 | 0 | 0 | 0 | 0 | 1 | 1 | 0 | 1 | 0 | 0 |
| 10 | 0 | 0 | 0 | 0 | 0 | 0 | 0 | 1 | 1 | 0 | 0 | 0 | 0 | 0 |
| 9  | 0 | 0 | 0 | 0 | 0 | 0 | 1 | 1 | 0 | 0 | 0 | 0 | 0 | 0 |
| 8  | 0 | 0 | 0 | 0 | 0 | 1 | 1 | 0 | 0 | 0 | 0 | 0 | 0 | 0 |
| 7  | 0 | 0 | 0 | 0 | 1 | 1 | 0 | 0 | 0 | 1 | 0 | 0 | 0 | 0 |
| 6  | 0 | 0 | 0 | 1 | 1 | 0 | 0 | 0 | 0 | 0 | 0 | 0 | 0 | 0 |
| 5  | 0 | 0 | 1 | 1 | 0 | 0 | 0 | 0 | 0 | 0 | 0 | 1 | 0 | 0 |
| 4  | 0 | 1 | 1 | 0 | 0 | 0 | 0 | 0 | 0 | 0 | 0 | 0 | 0 | 0 |
| 3  | 0 | 1 | 1 | 0 | 0 | 0 | 0 | 0 | 0 | 0 | 0 | 0 | 0 | 1 |
| 2  | 1 | 1 | 0 | 0 | 0 | 0 | 0 | 0 | 0 | 1 | 0 | 0 | 0 | 0 |
| 1  | 1 | 0 | 0 | 0 | 0 | 0 | 0 | 0 | 0 | 0 | 0 | 0 | 0 | 0 |

Database entry
mass 1464.497
Vertex array 0 1 1 1 1 1 1 1 1 1 1 1 1 1
Edge array 0 1 1 1 1 1 1 1 1 1 1 1 1 1

FIG. 17A

Database entry
mass 1494.07
Vertex array 1 1 1 1 1 1 1 1 1 1 1 0 1
Edge array 1 1 1 1 1 1 1 1 1 1 0 1 1 1

FIG. 17B

Database entry
mass 1393.46
Vertex array 0 1 1 1 1 1 1 1 1 1 1 0 1
Edge array 0 1 1 1 1 1 1 1 1 1 0 1 1 1

FIG. 17C

Database entry
mass 1583.555
Vertex array 1 1 1 1 1 1 1 1 1 1 1 1 1 1
Edge array 1 1 1 1 1 0 1 1 1 1 1 1 1 1

Database entry mass 1469.524

Vertex array 0 1 1 1 1 1 1 1 1 1 1 1 1

Edge array 0 1 1 1 1 1 1 1 1 1 1 1 1

FIG. 18B

Database entry mass 1354.481

Vertex array 1 1 1 1 1 1 1 1 1 1 0 1

Edge array 1 1 1 1 1 1 1 1 1 0 1 1 1

FIG. 18C

Database entry mass 1283.444

Vertex array 0 1 1 1 1 1 1 1 1 1 0 1

Edge array 0 1 1 1 1 1 1 1 1 0 1 1 1

FIG. 18D

Database entry mass 1301.455

Vertex array 0 1 1 1 1 1 1 1 1 1 1 0

Edge array 0 0 1 1 1 1 1 1 1 1 0 1 1 mw=1393.4600 order = 0; % "order" is the order in which a structure is entered into the database. "order" is incremented as the database grows. When "order" reaches 10^6, or the hard drive is close to filling in, a warning is given that a complete database cannot be constructed with the space available, and to please consider partitioning MCU graph into several subgraphs for e=1:numberOfEdges % ß- START by adding each individual edge present in the structure, to the database. Just the edge is added, with no neighbors. Therefore, the first several entries of the database will have a single "1" in the Edge array and two "1"'s in the Vertex array (because each edge connects two vertices).

order = order+1; % increment "order" to track number of entries in database

Edges(e)=1; % "Edges" binary vector, initially all 0's, gets a 1 for edge e
   Vertices = E2V(e,:); % Vertices binary vector, initially all 0's, gets two elements set to 1, specifically those vertices adjacent to edge "e"

% add substructure to database. The database is implemented as an
  % associative array, with edge indicator array acting as an index
  Record.Order = order;
  Record.Edges = Edges;
  Record.Vertices = Vertices
  SubstructureDatabase(Edges) = Record;

% recursively add DAUGHTER substructures of edge "e", to the database
  add_subgraphs(Edge_Occ, E2V(e,:), e, J(e,:));
  Edge_Occ(e)=0; % zero out Edge occurrence binary vector
end % for e end % main function add_subgraphs(parent_edge_subset,parent_edge_subset_str,parent_vert_subset, subset_min, neighbors)

% recursive step: For each substructure already in database ("parent substructure")
       - identify its neighbors,
       - add each ONE neighbor, one by one, to the parent substructure. This creates daughter substructures, that only differ from the parent substructure by one edge. Each daughter substructure is added to the database. The process repeats until there are no more substructures to add to the database.

for j=find(neighbors)
  child_edge_subset = parent_edge_subset;
  child_edge_subset(j)=1; % the only difference between child and parent subsets is one extra node
  if ~isKey(SubstructureDatabase,child_edge_subset_str)
    order = order+1;
    Record.Order = order;
    Record.Edges = child_edge_subset;
    % determine any new vertices
    f = find(E2V(j,:) & ~parent_vert_subset);
    child_vert_subset = parent_vert_subset;
    child_vert_subset(f)=1;
    Record.Vertices = child_vert_subset;
    SubstructureDatabase(child_edge_subset_str)=Record;
    neighbors_j = (neighbors | J(j,:)) & ~child_edge_subset
    add_subgraphs(child_edge_subset,child_edge_subset_str,child_vert_subset, subset_min, neighbors_j);
  end % if
end % for
end % function

FIG. 28

CUT VERTEX METHOD FOR IDENTIFYING COMPLEX MOLECULE SUBSTRUCTURES

FIELD OF THE INVENTION

The present invention relates to systems, apparatuses and methods for identifying substructures of complex molecules, particularly large molecules such as biomolecules, using a cut vertex approach.

BACKGROUND OF THE INVENTION

Identifying and characterizing substructures, such as metabolites, of pharmaceutical compounds is an important part of drug discovery. Understanding the structure of such metabolites and defining specific sites of metabolic transformations is useful, for example, in guiding synthetic optimization of the lead compounds of drug candidates to overcome stability and toxicity issues often associated with those compounds.

Current metabolite identification (MetID) approaches have been unable to systematically characterize metabolites of large molecules, such as therapeutic proteins and peptides (TPPs) from biological matrices without prior knowledge of their structure. While some off the shelf small molecule MetID software, such as MASSCAP, SEQUEST and Mass-MetaSite, are useful in characterizing metabolites of small molecule drugs and small linear peptides, this software has proven to be impractical or unsuitable for identifying metabolites and other substructures of larger biomolecules, such as large non-linear peptides/proteins. There are at least three reasons for this deficiency: (i) most small molecule MetID software cannot properly deconvolute monoisotopic peaks for large molecules, which results in incorrect input mass values; (ii) most small molecule MetID software uses an atom-based algorithm designed for small molecule drugs, and the number of atoms of a typical large biomolecule, such as a TPP, is typically 1-2 orders of magnitude higher than for small molecules, which introduces a huge computational complexity for such atom-based algorithms; and (iii) information that is useful for small molecule MetID, such as cytochrome P450 metabolism pathways or mass defect filters, does not apply to large molecules, as large molecules have distinct metabolic processes, which are not generally accounted for in conventional small molecule software.

The computational complexity associated with atom-based representation of molecules can hinder, or sometimes thwart, computer analysis. Depending on the amount of RAM in a given computer, the processing required to identify all of the metabolites of a molecule having more than 10 million metabolites would likely overwhelm the computer's processing capabilities. One gigabyte of RAM can, in the inventors' experience, handle about a million substructures. But a complex large molecule often contains over 10 million substructures, and indeed can often contain hundreds of millions of substructures.

In addition, conventional software for analyzing protein structure, such as proteomics-based software, for example, typically calculates amide and disulfide bond cleavages, and has been so far unable to address the unpredictable metabolism profiles of large molecules, such as TPPs, which includes unpredicted modifications (+Oxy, +P, +Met, etc.), non-natural amino acids, in vivo disulfide scrambling, non-natural linkers and nonspecific proteolytic cleavages.

Thus, there is considerable need for systems and processes that are capable of decoding nonlinear peptides for large molecules, particularly those large molecules that have a very large number of substructures, for example hundreds of millions of substructures, and for systems and methodology that not only facilitate differentiating metabolites of large molecules, such as therapeutic peptides or proteins, from the proteinaceous background in the biological matrix, but also facilitates elucidation of the structure of metabolites of interest. There is also considerable need for systems and processes that improve the functioning of conventional computer systems so as to permit those conventional computer system to do a better job of generating and displaying visual representations of the structures of large molecule metabolites on monitors and other display devices for viewing and analyzing by scientists and researchers.

SUMMARY OF THE INVENTION

In general, embodiments of the present invention may be used by scientists, such as chemists and biochemists, to identify metabolites and other substructures of complex molecules, and determine the associated chemical structures of such metabolites and other substructures. As such, embodiments of the present invention may be considered to be extremely useful in drug development and design. To this end, embodiments of the present invention employ a unique system for representing the molecules under study (the chosen molecule). Specifically, a chosen molecule is described in terms of a graph of defined minimum cleavable units, referred to as a minimum cleavable unit graph (an MCU graph). A minimum cleavable unit, as recited herein, is a part of a molecule where no cuts/cleavage (no metabolic process) are allowed to take place. The minimum cleavable unit may comprise a group of atoms between adjacent metabolic cleavage sites of a chosen molecule. By way of example, a minimum cleavable unit for a protein or peptide molecule may comprise a single amino acid, or a stretch of amino acids, for example. A minimum cleavable unit of a cyclic peptide may comprise a core region of the cyclic peptide, for example. The minimum cleavable unit approach facilitates defining molecules of interest in a simpler manner, for example, by reducing the complexity of a complex protein structure by attempting to reduce it to linear peptide realm. The minimum cleavable unit approach allows the user to define a module that eliminates follow up on metabolites that have cleavages within the MCU and are therefore not functional. Each MCU in the chosen molecule corresponds to a vertex in the MCU graph. The MCU graph is in turn represented by data stored in a data structure in the memory of the computer system.

A chosen molecule may have many different MCU graphs, depending on the goal of a given study and how the MCU is defined. For example, if the goal of the study is to identify all metabolites generated by amide bond cleavages, then the MCU is defined as each individual amino acid residue, because the user will consider no further metabolism beyond single amino acids. As another example, if the goal of a study is to identify active metabolites of a cyclic peptide, the cyclic region of the peptide would also be included as an MCU, since an active metabolite must have an intact cyclic region, and no further metabolism needs to be considered within the cyclic region.

The inventors of the present invention have recognized that line graphs derived from MCU graphs are an efficient way to identify substructures, such as metabolites, of molecules and are particularly useful in the substructure identification systems, apparatuses and methods of the present invention. The reason for this is that the universe of induced connected subgraphs of a line graph of an MCU graph completely and uniquely represents the entire universe of substructures and metabolites for the molecule represented by the corresponding MCU graph. In other words, there is a one-to-one relationship between the set of induced connected subgraphs of a line graph of an MCU graph and the set of metabolites for the molecule represented by the corresponding MCU graph. This relationship is actionable because it permits using an algorithm to identify the entire universe of metabolites of the chosen molecule. Practical application of the algorithm significantly improves the functioning of computer systems used to identify the entire universe of metabolites for the chosen molecule.

Commonly owned U.S. Pat. No. 11,854,664 describes a system and method for identifying substructures of complex molecules, wherein the system and method involves generating a database comprising thousands or millions of records corresponding, respectively, to thousands or millions of substructures of a chosen molecule. There are some large molecules, however, that have hundreds of millions, or even billions, of substructures, which cannot be processed and identified on a conventional personal computer system with conventional central processing units and conventional memory devices without overtaxing the computer system and potentially causing the computer system to get hung up or stop functioning altogether.

As will be described in more detail below, embodiments of the present invention avoid this problem by receiving and storing data representing the minimum cleavable unit (MCU) graph for a chosen molecule, as well as a specified "cut vertex" in the MCU graph for the chosen molecule. The system then splits the MCU graph of the chosen molecule at the specified cut vertex to produce two separate MCU graph components (i.e., a first MCU subgraph and a second MCU subgraph) of the chosen molecule. The system then generates a first line graph component and a second line graph component, respectively, for the two MCU subgraph components, traverses the first line graph component with a graph traversing algorithm to generate and store in memory a first database of substructures and molecular weights for the first component, and then traverses the second line graph component with the graph traversing algorithm to build and store in the memory a second database of substructures and molecular weights for the second line graph component. Alternatively, the system may be configured to put the substructures and molecular weights for both the first line graph component and the second line graph component in a single database, or a plurality of databases, without departing from the main principles of operation of the invention.

Subsequently, with the substructures and molecular weights for the first line graph component and the second line graph component stored in one or more databases in the memory of the computer system (or in two subsections of a single database, if preferred), embodiments of the present invention are capable of receiving a query molecular weight (or a range of query molecular weights) from a user, and performing binary searches on the two databases (or the two subsections of a single database) to identify, retrieve and display graphic representations of all of the substructures of the chosen molecule that have molecular weights that match the query molecular weight (or range of query molecular weights), including the substructures of the chosen molecule that straddle (i.e., include) the cut vertex. Thus, the cut vertex approach described herein may be used to dynamically identify, produce and display all of the substructures of a chosen molecule having molecular weights that match a specified given molecular weight, regardless of whether the substructure with the specified given molecular weight exists completely within the first MCU graph component of the chosen molecule, completely within the second MCU graph component of the chosen molecule, or partially within both of the two MCU graph components of the chosen molecule (i.e., those substructures of the chosen molecule that have vertices and bonds that reside on both sides of the cut vertex in the MCU graph). In preferred embodiments, the substructures matching the given query molecular weight are listed and/or displayed in ranked order according to the number of biotransformations (i.e., broken covalent bonds) that would have to occur for the chosen molecule to be transformed into the matching substructure.

While describing various embodiments of the invention in this disclosure, reference is made to the use of two different databases to store substructures and molecular weights of substructures and to store induced connected subgraph records and biotransformation counts, it should be noted that the invention also encompasses using a single database for storing such information and records. In the case of a single database, it would be beneficial to use a substructure identifier that identifies whether a particular record in the subgraph database is associated with the first component or the second component of the line graph for the chosen molecule.

The cut vertex method is particularly useful for large molecules which contain multiple disulfide bonds and/or artificial linkers. The method is also particularly suitable for large molecules that have hundreds of millions of metabolites, such as dimers and other oligomers and multimers. Exemplary large molecules include, but are not limited to, antibodies, multimers of large molecules (such as dimers, trimers, tetramers and polymers) as well as conjugated molecules.

In addition to being useful for identifying and analyzing the substructures of large molecules, however, embodiments of the present invention are also useful for identifying and analyzing the substructures of small molecules. Small molecules may include organic molecules that have a relatively low molecular weight, whether naturally-occurring or artificially created (e.g., via chemical synthesis). Embodiments of the present invention are also useful for analyzing small molecules that are biologically active in that they produce a local or systemic effect in animals, preferably mammals, more preferably humans. In certain embodiments, the small molecule has a molecular weight of less than or equal to about 900 Daltons. The present inventors have discovered that the cut vertex approach is particularly useful in cases where the number of induced connected subgraphs (i.e., substructures) of a chosen molecule exceeds, or is expected to exceed, available computer memory, though the approach is useful even in situations where the number of substructures of a given chosen molecule is not particularly high or is not expected to exceed computer memory.

Beneficially, the cut vertex approach of the present invention is very flexible in that it does not require following a rigid set of rules to select and identify an appropriate cut vertex in the MCU graph representing the chosen molecule. In other words, recognizing and identifying a suitable cut vertex for the chosen molecule may be accomplished using any one of a variety of different techniques, including, for example, the simple expedient of picking a point in the MCU graph that the user perceives is located roughly at or somewhere near the middle of the MCU graph.

Building a Database of Induced Connected Subgraph Records Representing the Substructures Existing in Each of the Two Components of the MCU Graph In a first phase of operation of one embodiment of the invention, the user inputs chosen molecule data, comprising (A) one or more sets of minimum cleavable units for the components of the chosen molecule, (B) one or more sets of bonds connecting the set of minimum cleavable units in the components of the chosen molecule, (C) molecular weights for each minimum cleavable unit, and (D) a connectivity profile for the chosen molecule. The connectivity profile is arranged to indicate the relative positions of minimum cleavable units and bonds, and the connections between minimum cleavable units and bonds. The chosen molecule data may be provided in the form of an MCU graph of the chosen molecule or another representation of a chosen molecule, such as a chemical structure or drawing with vertex and edge annotations that include identification of the MCUs, the types of bonds connecting the MCUs, and the molecular weights of each one of the MCUs.

The user also identifies one of the MCUs as the cut vertex for the chosen molecule. Although it is not actually removed, removal of the cut vertex from an MCU graph of the chosen molecule would split (or separate) the MCU graph of the chosen molecule into two components (i.e., two MCU subgraphs), not counting the cut vertex itself. However, both of the two components include the cut vertex. The two components will be referred to in this disclosure as the first component and the second component, respectively, of the MCU graph for the chosen molecule, or alternatively referred to as two MCU subgraphs, both of which include the cut vertex MCU. The two connected MCU subgraphs are not necessarily equal in size; nor are the two connected MCU subgraphs necessarily equal in the numbers of vertices and bonds, although they could be equal in size and the numbers of vertices and bonds.

In embodiments of the present invention, the system uses the chosen molecule data to create and store in memory an MCU graph data structure for each one of the two components of the chosen molecule defined by the location of the cut vertex MCU. Suitable MCU graph data structures may include, without limitation, arrays, adjacency matrices, adjacency lists, incidence matrices or incidence lists, as well as any other computer data structure capable of holding MCU graph data. Based on the MCU graph data structure for each one of the two components of the chosen molecule, the system then generates line graph data representing a line graph of each one of the two components of the MCU graph for the chosen molecule, and stores the line graph data in two individual line graph data structures, respectively, in memory, as will be described in more detail below. Suitable line graph data structures may include adjacency matrices, adjacency lists, incidence matrices or incidence lists, for example.

The system then traverses the line graph data in the first line graph data structure for the first component of the MCU graph for the chosen molecule using a suitable graph traversal algorithm (an example of which is shown in FIG. 29) to identify and record in memory vertex and edge data for every induced connected subgraph (ICS) for the line graph of the first component of the MCU graph. Then the system traverses the line graph data in the second line graph data structure for the second component of the MCU graph for the chosen molecule (typically, but not necessarily, using the same graph traversal algorithm) to identify and record in memory vertex and edge data for every induced connected subgraph (ICS) for the line graph of the second component of the MCU graph. Suitable graph traversal algorithms include a depth-first search algorithm, or a breadth-first search algorithm, or a reverse-search algorithm, or a tree-search algorithm, or a combination of two of more of the graph traversal algorithms recited herein.

For each ICS identified by executing the graph traversal algorithm on the line graph data, the system creates an ICS record in memory, the ICS record containing a molecular weight field, a vertex data field and an edge data field. The system then calculates and stores a molecular weight corresponding to each ICS and stores the molecular weight in the molecular weight field alongside the vertex and edge data for each ICS record, so that each ICS record can subsequently be searched according to the values in the molecular weight fields. Preferably, the system also calculates and stores in each ICS record the number of biotransformations (i.e., the biotransformation count) that would be required to transform the chosen molecule into the substructure represented by the vertex data, the edge data and the molecular weight for that ICS record. Storing the biotransformation counts alongside the other data in each ICS records permits searching and/or ranking the search results according to the biotransformation counts.

The result of executing the graph traversal algorithm against the line graph data for both the first component of the MCU graph and the second component of the MCU graph during the first phase of operation is that, at the end of the first phase of operation, the memory will contain a plurality of ICS records for the first component of the MCU graph for the chosen molecule, as well as a plurality of ICS records for the second component of the MCU graph for the chosen molecule. Every ICS record for the first component contains vertex data, edge data and molecular weight data representing the structure, weight and physical layout of every substructure in the first component of the chosen molecule, including the cut vertex, and every ICS record for the second component contains vertex data, edge data and molecular weight data representing the structure, weight and physical layout of every substructure in the second component of the chosen molecule, including the cut vertex. Thus, at this point, the memory will contain an ICS record for every induced connected subgraph that exists entirely within the first component of the MCU graph, and an ICS record for every induced connected subgraph that exists entirely within the second component of the MCU graph.

Notably, the system does not need to create, and the memory does not need to store, any ICS records for any induced connected subgraphs having vertices and bonds in both the first component and the second component of the MCU graph. Nevertheless, as will be described in more detail below, in a subsequent phase of operation, the system is capable of identifying and displaying a graphical representation of (1) any induced connected subgraph existing in the first component of the chosen molecule, (2) any induced connected subgraph existing in the second component of the chosen molecule, and (3) any induced connected subgraph having constituent parts simultaneously existing in both components of the chosen molecule (i.e., straddling the cut vertex MCU so that vertices exist in both components of the MCU graph for the chosen molecule).

Identifying the Substructures with a Given Molecular Weight, which Exist in Either the First Component or the Second Component of the MCU Graph for the Chosen Molecule, but not Both In a second phase of operation, the system receives a query molecular weight from a user (who may or may not be the user who provided the chosen molecule data), wherein the query molecular weight entered is pre-determined by the user, either by experimentation or obtained from another source or device, such as a mass spectrometer. The system searches the ICS records that are stored in the memory (each ICS containing a molecular weight, vertex array values, edge array values and biotransformation counts) to find all of the ICS records for the first and second components of the chosen molecule that have a total molecular weight in the molecular weight field that matches the query molecular weight. When such ICS records are found, the system uses the information in the ICS records to produce and display to the user vertex and edge data for each induced connected subgraph for each ICS record found. Optionally, the system may also display, print or transmit a graphical representation of the structure of the matching induced connected subgraph based on the vertex and edge data in each record.

Thus, at this point, the system will have produced, transmitted and/or displayed vertex data, edge data and/or a graphical representation for any induced connected subgraph in the first component of the MCU graph for the chosen molecule (i.e., every substructure in the first component of the chosen molecule), as well as vertex data, edge data and/or a graphical representation for any induced connected subgraph in the second component of the MCU graph for the chosen molecule (i.e., every substructure in the second component of the chosen molecule), which have a mass that matches the query mass. Preferably, the search results are ranked and displayed in order of ascending biotransformation counts so that the induced connected subgraphs requiring the least number of biotransformations are displayed first (i.e., at the top of the list and before the matching induced connected subgraphs requiring higher numbers of biotransformations.

Identifying the Substructures with the Given Molecular Weight, which Exist in Both the First Component and the Second Component of the MCU Graph for the Chosen Molecule In a third phase of operation, the system searches the ICS records in the memory again to find a combination of two ICS records (one record for each component of the chosen molecule) that have molecular weights that, when combined, have a total molecular weight that matches the query molecular weight. If such a combination of molecular weights is found, it means that there exists a substructure for the chosen molecule, which corresponds to the structure and physical arrangement of vertices and bonds in an induced connected subgraph that straddles (includes) the cut vertex, and has vertices existing in both the first and second components. In preferred embodiments, the invention is also configured to transmit and/or display on a display device the vertex data, the edge data (and optionally a graphical representation) for the substructure of the chosen molecule that straddles and includes the cut vertex.

In one embodiment of the invention, searching the ICS records in the memory to find two induced connected subgraphs that are linked to each other through the cut vertex, and which together have a total molecular weight matching the query molecular weight, is carried out as follows. The system first calculates an adjusted query molecular weight by subtracting the molecular weight of the cut vertex from the query molecular weight, and then searches the ICS records for the first component to identify ICS records that have a molecular weight in the molecular weight field that matches the adjusted query molecular weight. The system then identifies the ICS record for the first component of the chosen molecule that has the lowest molecular weight in the molecular weight field. This lowest molecular weight is then subtracted from the adjusted query molecular weight to provide a modified query molecular weight. The modified query molecular weight is used to perform a binary search of the ICS records for the second component to identify an ICS record for the second component that has a molecular weight in the molecular weight field that, when combined with the lowest molecular weight of the ICS record for the first component of the chosen molecule, matches the modified query molecular weight. If a match is found, the system displays, prints and/or transmits to a display device accessible by the user the vertex and edge information in the identified ICS record for the first component, as well as the vertex and edge information in the identified ICS record for the second component. Optionally, the system may also display, print or transmit a graphical representation of the cut-vertex-straddling substructure by concatenating a graphical representation of the identified ICS of the first component with a graphical representation of the identified ICS of the second component, thereby producing a graphical representation of a substructure of the chosen molecule, wherein the substructure includes the cut vertex and vertices on each side of the cut vertex.

The system repeats the search of the database to identify the ICS record for the first component of the chosen molecule that has the next lowest molecular weight relative to the remaining pool of ICS records in the first database for the first component of the chosen molecule, calculates a new modified query molecular weight, and uses the newly calculated modified query molecular weight to perform a binary search of the ICS records for the second component of the chosen molecule that have a molecular weight in the molecular weight field that, when combined with the next lowest molecular weight of the ICS record for the first component of the chosen molecule, matches the modified query molecular weight. The process is repeated until the molecular weights of all of the ICS records for the first component of the MCU graph for the chosen molecule have been used to calculate modified molecular weights and facilitate a search of the ICS records for the second component of the MCU graph for the chosen molecule. If a match is found, the system displays, prints or transmits information in the identified ICS records (for the first component and the second component) to a display device operated by the user. Optionally, the system may also display, print or transmit a graphical representation of the combined substructure for the matching induced connected subgraphs from both the first and second components based on the vertex and edge data in each record, wherein the combined substructure includes the cut vertex and vertices on both sides of the cut vertex.

Consistent with the operations described above, there are several potential implementations of the invention. In one implementation, the invention provides a system for identifying substructures of a chosen molecule, the system comprising a microprocessor, a memory, an application program in the memory, and a user interface in the memory for communication with an end user. The application program and the user interface both comprise program instructions that, when executed by the microprocessor, will cause the microprocessor to:

1) receive and store in the memory chosen molecule data representing (A) a set of minimum cleavable units in the chosen molecule, (B) a set of bonds connecting the set of minimum cleavable units in the chosen molecule, (C) molecular weights for each minimum cleavable unit, (D) a connectivity profile for the chosen molecule, the connectivity profile indicating relative positions of minimum cleavable units and bonds and connections therebetween; and (E) a cut vertex in the chosen molecule, wherein removal of the cut vertex would separate the chosen molecule into a first component and a second component;

2) based on the chosen molecule data, create and store in the memory a first minimum cleavable unit graph data structure for the first component of the chosen molecule, the first minimum cleavable unit graph data structure being populated with first MCU graph data representing a first MCU graph for the first component, the first MCU graph having a plurality of first MCU graph vertices and a plurality of first MCU graph edges, each first MCU graph vertex corresponding to a minimum cleavable unit of the first component and each first MCU graph edge corresponding to a first bond connecting minimum cleavable units in the first component;

3) based on the first MCU graph data, generate and store in the memory a first line graph data structure for the first component of the chosen molecule, the first line graph data structure being populated with first line graph data representing a first line graph for the first MCU graph, the first line graph having a plurality of first line graph vertices and a plurality of first line graph edges, each first line graph vertex ("LG vertex") corresponding to a first MCU graph edge in the first MCU graph and each first line graph edge ("LG edge") corresponding to a pair of first MCU graph vertices in the first MCU graph that are connected together by said first MCU graph edge;

4) execute a graph traversal algorithm against the first line graph data in the first line graph data structure for the first component of the chosen molecule to determine a plurality of first induced connected subgraphs for the first line graph, each first induced connected subgraph comprising a first connected subset of first LG vertices and first LG edges in the first line graph, and a first physical arrangement of said first connected subset of first LG vertices and first LG edges, wherein the connected subset of first LG vertices and first LG edges, together with the first physical arrangement thereof uniquely corresponds to a first connected subset of the set of minimum cleavable units and bonds, and the relative positions of said first connected subset of minimum cleavable units and bonds in the chosen molecule;

5) for each first induced connected subgraph represented in the first line graph data structure for the first component of the chosen molecule, create and store in a database a first ICS record comprising a first molecular weight field, a first vertex data field and a first edge data field, wherein the first vertex data field is populated with first vertex values configured to indicate a first vertex position for every first LG vertex in the first induced connected subgraph, and the first edge data field is populated with first edge values configured to indicate the first edge position of every first LG edge in the first induced connected subgraph relative to the first LG vertices; and 6) for each first ICS record in the first line graph data structure for the first component of the chosen molecule, calculate and store in the first molecular weight field a first total molecular weight for the first induced connected subgraph of that first ICS record based on the chosen molecule data for the chosen molecule and the first vertex values and the first edge values in the first ICS record;

7) based on the chosen molecule data, create and store in the memory a second minimum cleavable unit graph data structure for the second component of the chosen molecule, the second minimum cleavable unit graph data structure being populated with second MCU graph data representing a second MCU graph for the second component, the second MCU graph having a plurality of second MCU graph vertices and a plurality of second MCU graph edges, each second MCU graph vertex corresponding to a minimum cleavable unit of the second component and each second MCU graph edge corresponding to a second bond connecting minimum cleavable units in the second component;

8) based on the second MCU graph data, generate and store in the memory a second line graph data structure for the second component of the chosen molecule, the second line graph data structure being populated with second line graph data representing a second line graph for the second MCU graph, the second line graph having a plurality of second LG vertices and a plurality of second LG edges, each second LG vertex corresponding to a second MCU graph edge in the second MCU graph and each second LG edge corresponding to a pair of second MCU graph vertices in the second MCU graph that are connected together by said second MCU graph edge;

9) execute the graph traversal algorithm against the second line graph data in the second line graph data structure for the second component of the chosen molecule to determine a plurality of second induced connected subgraphs for the second line graph, each second induced connected subgraph comprising a second connected subset of second LG vertices and second LG edges in the second line graph, and a second physical arrangement of said second connected subset of second LG vertices and second LG edges, that together uniquely corresponds to a second connected subset of the set of minimum cleavable units and bonds, and the relative positions of said second connected subset of minimum cleavable units and bonds in the chosen molecule;

10) for each second induced connected subgraph represented in the second line graph data structure for the second component of the chosen molecule, create in the database a second ICS record comprising a second molecular weight field, a second vertex data field and a second edge data field, wherein the second vertex data field is populated with second vertex values configured to indicate a second vertex position for every second LG vertex in the second induced connected subgraph, and the second edge data field is populated with second edge values configured to indicate the second edge position of every second LG edge in the second induced connected subgraph relative to the second LG vertices; and 11) for each second ICS record in the second line graph data structure for the second component of the chosen molecule, calculate and store in the second molecular weight field a second total molecular weight for the second induced connected subgraph of that second ICS record based on the chosen molecule data for the chosen molecule and the second vertex values and the second edge values in the second ICS record.

The user interface includes program instructions that, when executed by the microprocessor, will cause the microprocessor to:
(i) receive a query molecular weight from the end user,
(ii) search the database to identify a first ICS record having a first total molecular weight in the first molecular weight field that matches the query molecular weight, (iii) search the database to identify a second ICS record having a second total molecular weight in the second molecular weight field that matches the query molecular weight, (iv) use the first vertex values in the first vertex data field and the first edge values in the first edge data field of the identified first ICS records to produce and display on a display device a first graphical representation of the first induced connected subgraph corresponding to the first ICS record having the first total molecular weight that matches the query molecular weight, (v) use the second vertex values in the second vertex data field and the second edge values in the second edge data field of the identified second ICS records to generate and display on the display device a second graphical representation of the second induced connected subgraph corresponding to the second ICS record having the second total molecular weight that matches the query molecular weight;

(vi) calculate an adjusted query molecular weight by subtracting a molecular weight for the cut vertex from the query molecular weight;

(vii) identify, for the first component of the chosen molecule, a first partial ICS record, the first partial ICS record having the lowest first molecular weight in the first molecular weight field relative to all the other molecular weights in the all the other molecular weight fields for the first component;

(viii) calculate a modified query molecular weight by subtracting the lowest first molecular weight of the first partial ICS record for the first component of the chosen molecule from the adjusted query molecular weight;

(ix) use the modified query molecular weight to search the ICS records for the second component of the chosen molecule to identify a second partial ICS record for the second component of the chosen molecule, the second partial ICS record having a second molecular weight in the second molecular weight field that, when combined with the first molecular weight of the first partial ICS record for the first component, matches the modified query molecular weight;

(x) use the vertex values in the vertex data fields for the first and second partial ICS records, the edge values in the edge data fields for the first and second partial ICS records, the cut vertex and the chosen molecule data to generate and display on the display device a graphical representation of a combined induced connected subgraph for the first and second components of the chosen molecule, wherein the combined induced connected subgraph is produced by concatenating together an induced connected subgraph for the first partial ICS record and an induced connected subgraph for the second partial ICS record;

(xi) replace the first partial ICS record with another first ICS record, wherein said another first ICS record comprises the next lowest first molecular weight in the first molecular weight field relative to molecular weight in the molecular weight field of the first partial ICS record; and (xii) repeat steps viii through xi above until each of the first molecular weights in the first molecular weight fields of the first ICS records for the first component of the chosen molecule have been used to carry out the steps viii-xi.

In additional embodiments of the invention, the system further comprises program instructions in the application program that, when executed by the microprocessor, causes the microprocessor to a) receive a specified tolerance for the query molecular weight, b) use the specified tolerance to calculate and define a range of molecular weights for the search of the database, c) search the database based on the query molecular weight and the range to identify each ICS record in the database that has a total molecular weight in the molecular weight field that falls within the defined range of molecular weights, and d) for said each identified ICS record, transmit the vertex values in the vertex data field and the edge values in the edge data field to the user interface for presentation to the end user; e) calculate an adjusted query molecular weight by subtracting the molecular weight of the cut vertex from the query molecular weight; f) identify the ICS record, for the first component of the chosen molecule, having the lowest molecular weight; g) calculate a modified query molecular weight by subtracting the lowest molecular weight of the ICS record for the first component of the chosen molecule from the adjusted query molecular weight; h) using the modified query molecular weight, perform a binary search of the ICS records for the second component of the chosen molecule to identify an ICS record that, when combined with the molecular weight of the ICS record for the first component, matches the modified query molecular weight; i) transmit the vertex values in the vertex data field and the edge values in the edge data field for the identified ICS record to the user interface for presentation on a display device operated by the end user; j) identify the ICS record for the first component of the chosen molecule that has the next lowest molecular weight; k) repeat steps g) through j) until each of the molecular weights for the ICS records for the first component of the chosen molecule have been used in steps g)-j).

In some embodiments of the invention, the chosen molecule data is obtained by executing instructions in the application program, which are configured to parse information stored in the memory of the computer system as a linked list, or an array, or an adjacency matrix, or a graphic image file, or a chemical drawing file (for example ChemDraw® file from Cambridge Soft®, PerkinElmer, Inc., Waltham, MA, USA), or a spreadsheet file, or a text file, or a CSV file, or a .CDX file, or a .CDXML file, or a .MOL file, or a .SDM file, or a CAD file, or a binary data file, or a .SMI file, or a .HELM file, or a .CHELM file, or a .XHELM file. The connected subset of the set of minimum cleavable units and bonds may comprise a metabolite of the chosen molecule, or a catabolite of the chosen molecule, or a gas phase fragmentation of the chosen molecule, or a degradant of the chosen molecule, or a substructure of the chosen molecule.

In some embodiments of the invention, the chosen molecule data includes elemental composition data representing (A) a set of elemental units in each minimum cleavable unit, (B) a set of elemental bonds connecting the set of elemental units in the minimum cleavable unit, (C) elemental molecular weights for each elemental unit, (D) an MCU connectivity profile for the minimum cleavable unit, the MCU connectivity profile indicating relative positions of elemental units and elemental bonds in the minimum cleavable units and connections therebetween, and E) a cut vertex in the chosen molecule. In these embodiments, the ICS record created in the database further comprises an elemental unit field populated with one or more elemental unit identifiers. The application program further includes program instructions that, when executed by the microprocessor, will cause the microprocessor to (a) receive a query elemental unit from the end user, (ii) search the database based on the query elemental unit to identify an ICS record having an elemental unit identifier in the elemental unit field that matches the query elemental unit, and (iii) transmit the vertex values in the vertex data field and the edge values in the edge data field for the identified ICS record to the user interface for presentation on a display device operated by the end user.

In another implementation, the invention provides a system for generating a database to facilitate identifying substructures of a chosen molecule using a microprocessor, the system comprising a primary memory, a secondary memory, a microprocessor, an input module, an MCU graph data structure generator, a line graph data structure generator, a graph traversing module, a subgraph database, and a molecular weight calculator.

The input module comprises program instructions configured to cause the microprocessor to receive and store chosen molecule data representing (A) a set of minimum cleavable units in the chosen molecule, (B) a set of bonds connecting the set of minimum cleavable units in the chosen molecule, (C) molecular weights for each minimum cleavable unit, and (D) a cut vertex located within the chosen molecule, wherein removal of the cut vertex separates the chosen molecule into a first and a second component, and (E) a connectivity profile for the minimum cleavable units and the bonds in the chosen molecule, the connectivity profile indicating relative positions of minimum cleavable units and bonds and connections therebetween.

The MCU graph data structure generator comprises program instructions configured to cause the microprocessor to create and store in the memory i) a first minimum cleavable unit graph data structure for the first component of the chosen molecule, and ii) a second minimum cleavable unit graph data structure for the second component of the chosen molecule. The first minimum cleavable unit graph data structure is populated with first MCU graph data representing a first MCU graph for the first component. The first MCU graph comprises a plurality of first MCU graph vertices and a plurality of first MCU graph edges, each first MCU graph vertex corresponding to a minimum cleavable unit of the first component and each first MCU graph edge corresponding to a first bond connecting minimum cleavable units in the first component. The second minimum cleavable unit graph data structure is populated with second MCU graph data representing a second MCU graph for the second component, the second MCU graph having a plurality of second MCU graph vertices and a plurality of second MCU graph edges. Each second MCU graph vertex corresponds to a minimum cleavable unit of the second component and each second MCU graph edge corresponds to a second bond connecting minimum cleavable units in the second component.

The line graph data structure generator includes program instructions executable on the microprocessor to generate and store in the memory a first line graph data structure for the first component of the chosen molecule based on the first MCU graph data. The first line graph data structure is populated with first line graph data representing a first line graph for the first MCU graph, wherein the first line graph has a plurality of first LG vertices and a plurality of first LG edges, each first LG vertex corresponding to a first MCU graph edge in the first MCU graph and each first LG edge corresponding to a pair of first MCU graph vertices in the first MCU graph that are connected together by the first MCU graph edge. The line graph data structure generator also includes program instructions executable by the microprocessor to generate and store in the memory a second line graph data structure for the second component of the chosen molecule based on the second MCU graph data. The second line graph data structure is populated with second line graph data representing a second line graph for the second MCU graph, wherein the second line graph has a plurality of second LG vertices and a plurality of second LG edges, each second LG vertex corresponding to a second MCU graph edge in the second MCU graph and each second LG edge corresponding to a pair of second MCU graph vertices in the second MCU graph that are connected together by said second MCU graph edge.

The graph traversing module includes program instructions that are executable on the microprocessor to run a graph traversal algorithm against the first line graph data in the first line graph data structure for the first component of the chosen molecule to determine a plurality of first induced connected subgraphs for the first line graph, each first induced connected subgraph comprising a first connected subset of first LG vertices and first LG edges in the first line graph, and a first physical arrangement of the first connected subset of first LG vertices and first LG edges, that together uniquely corresponds to a first connected subset of the set of minimum cleavable units and bonds, and the relative positions of said first connected subset of minimum cleavable units and bonds in the chosen molecule.

The graph traversing module also includes program instructions executable on the microprocessor to run the graph traversal algorithm against the second line graph data in the second line graph data structure for the second component of the chosen molecule to determine a plurality of second induced connected subgraphs for the second line graph, each second induced connected subgraph comprising a second connected subset of second LG vertices and second LG edges in the second line graph, and a second physical arrangement of said second connected subset of second LG vertices and second LG edges, wherein the second connected subset of second LG vertices and second LG edges, together with the physical arrangement thereof, uniquely corresponds to a second connected subset of the set of minimum cleavable units and bonds, and the relative positions of said second connected subset of minimum cleavable units and bonds in the chosen molecule.

The subgraph database generator includes program instructions that cause the microprocessor to create in a subgraph database, for each first induced connected subgraph represented in the first line graph data structure for the first component of the chosen molecule, a first ICS record comprising a first molecular weight field, a first vertex data field and a first edge data field. The first vertex data field is populated with first vertex values configured to indicate a first vertex position for every first LG vertex in the first induced connected subgraph, and the first edge data field is populated with first edge values configured to indicate the first edge position of every first LG edge in the first induced connected subgraph relative to the first LG vertices. The database generator also includes program instructions that cause the microprocessor to create in the subgraph database, for each second induced connected subgraph represented in the second line graph data structure for the second component of the chosen molecule, a second ICS record comprising a second molecular weight field, a second vertex data field and a second edge data field. The second vertex data field is populated with second vertex values configured to indicate a second vertex position for every second LG vertex in the second induced connected subgraph, and the second edge data field is populated with second edge values configured to indicate the second edge position of every second LG edge in the second induced connected subgraph relative to the second LG vertices.

The molecular weight calculator includes program instructions cause the microprocessor to calculate and store in the first molecular weight field, for each first ICS record in the first line graph data structure for the first component of the chosen molecule, a first total molecular weight for the first induced connected subgraph of that first ICS record based on the elemental molecular weights provided by the chosen molecule data for the chosen molecule, and the first vertex values and the first edge values in the first ICS record. The molecular weight calculator also includes program instructions to cause the microprocessor to calculate and store in the second molecular weight field, for each second ICS record in the second line graph data structure for the second component of the chosen molecule, a second total molecular weight for the second induced connected subgraph of that second ICS record based on elemental molecular weights provided by the chosen molecule data for the chosen molecule, and the second vertex values and the second edge values in the second ICS record.

In yet another implementation of the invention, there is provided a computer-implemented method for generating a database in memory to facilitate identifying substructures of a chosen molecule using a microprocessor, a memory device and a display device. In the first step, the method receives and stores in the memory device chosen molecule data representing (A) a set of minimum cleavable units in the chosen molecule, (B) a set of bonds connecting the set of minimum cleavable units in the chosen molecule, (C) molecular weights for each minimum cleavable unit, and (D) a cut vertex located within the chosen molecule, wherein removal of the cut vertex separates the chosen molecule into a first component and a second component, and (E) a connectivity profile for the chosen molecule, the connectivity profile indicating relative positions of minimum cleavable units and bonds and connections therebetween, Next, based on the chosen molecule data, the computer implemented method creates and stores in the memory device a minimum cleavable unit graph data structure for the first component and the second component of the chosen molecule. The minimum cleavable unit graph data structure is populated with MCU graph data representing an MCU graph for the chosen molecule. The MCU graph has a plurality of MCU graph vertices and a plurality of MCU graph edges, each MCU graph vertex corresponding to a minimum cleavable unit of the chosen molecule and each MCU graph edge corresponding to a bond connecting minimum cleavable units in the chosen molecule.

Based on the MCU graph data, a first line graph data structure for the first component of the chosen molecule and a second line graph data structure for the second component of the chosen molecule are generated and stored in the memory device. Each line graph data structure is populated with line graph data representing a line graph for the first and second components of the MCU graph. The first and second line graphs each have a plurality of LG vertices and a plurality of LG edges, each LG vertex corresponding to an MCU graph edge in the MCU graph and each LG edge corresponding to a pair of MCU graph vertices in the MCU graph that are connected together by said MCU graph edge.

In the next step of the method, the microprocessor is used to run a graph traversal algorithm against the first line graph data in the first line graph data structure for the first component of the chosen molecule and the second line graph data in the second line graph data structure for the second component of the chosen molecule to determine, for each component (a) a plurality of induced connected subgraphs for the line graph, each induced connected subgraph comprising a connected subset of LG vertices and LG edges in the line graph, (b) a physical arrangement of the connected subset of LG vertices and LG edges that together uniquely corresponds to a connected subset of the set of minimum cleavable units and bonds, and (c) the relative positions of the connected subset of minimum cleavable units and bonds in the chosen molecule.

For each induced connected subgraph represented in the first line graph data structure for the first component and each second line graph data structure for the second component, the method further comprises the steps of creating in the subgraph database an ICS record comprising a molecular weight field, a vertex data field and an edge data field, wherein the vertex data field is populated with vertex values configured to indicate a vertex position for every LG vertex in the induced connected subgraph, and the edge data field is populated with edge values configured to indicate the edge position of every LG edge in the induced connected subgraph relative to the LG vertices. For each ICS record in the line graph data structure for the first component and the second component of the chosen molecule, the microprocessor is used to calculate and store in the molecular weight field a total molecular weight for the induced connected subgraph of that ICS record based on the chosen molecule data for the chosen molecule and the vertex values and the edge values in the ICS record.

In some embodiments of the invention, the method further comprises a) receiving a query molecular weight by the microprocessor; b) with the microprocessor, searching the subgraph database based on the query molecular weight to identify an ICS record having in the molecular weight field a total molecular weight that matches the query molecular weight; c) transmitting a representation of the vertex values in the vertex data field and the edge values in the edge data field for the identified ICS record to a display device; (d) calculating an adjusted query molecular weight by subtracting the molecular weight of the cut vertex from the query molecular weight; (e) identifying the ICS record for the first component of the chosen molecule, having the lowest molecular weight; (f) calculating a modified query molecular weight by subtracting the lowest molecular weight of the ICS record for the first component of the chosen molecule from the adjusted query molecular weight; (g) using the modified query molecular weight to perform a binary search of the ICS records for the second component of the chosen molecule to identify an ICS record that, when combined with the molecular weight of the ICS record for the first component, matches the modified query molecular weight; (h) transmitting the vertex values in the vertex data field and the edge values in the edge data field for the identified ICS record to the user interface for presentation on a display device operated by the end user; (i) identifying the ICS record for the first component of the chosen molecule that has the next lowest molecular weight; and (j) repeating steps f) through h) until each of the molecular weights for the ICS records for the first component of the chosen molecule have been used in steps f) through i).

In some embodiments the invention, the connected components of the line graph G, (potential metabolites of the original molecule) are determined by a formula:

i) a subgraph of $G_1 \backslash \{v\}$;

ii) a subgraph of $G_2 \backslash \{v\}$; or (iii) a subgraph $C_1 \cup \{v\} \cup C_2$, wherein C₁ and C₂ are subgraphs of G₁\{v} and G₂\{v}, respectively, and are adjacent to vertex v.

BRIEF DESCRIPTION OF THE DRAWINGS

FIG. 9A illustrates a Minimum Cleavable Unit Graph of a hypothetical chosen molecule containing a cut vertex (Q) that may be generated by the process of FIG. 7.

FIG. 9B illustrates data structures (adjacency matrices) of the two components of a hypothetical chosen molecule generated in accordance with an embodiment of the invention.

FIG. 9C illustrate two exemplary line graphs that may be generated to represent the components of the hypothetical chosen molecule.

FIG. 9D shows two exemplary line graph data structures, namely adjacency matrices, of the line graph shown in FIG. 9C.

FIG. 13 is an Edge to Vertex data structure which may be generated in accordance with an embodiment of the invention to represent the first monomer of the synthetic dimer shown in FIG. 10.

FIG. 17A-17D are exemplary subgraph database records of monomer A generated in accordance with an embodiment of the invention.

FIGS. 18A-18D are exemplary subgraph database records of monomer B generated in accordance with an embodiment of the present invention.

FIG. 28 shows exemplary MatLab program instructions for a graph traversal algorithm that, when executed by a microprocessor, will cause the microprocessor to populate a subgraph database from MCU graph data stored in an MCU graph adjacency matrix in accordance with an embodiment of the present invention.

DETAILED DESCRIPTION OF EXEMPLARY EMBODIMENTS

Figure 1:
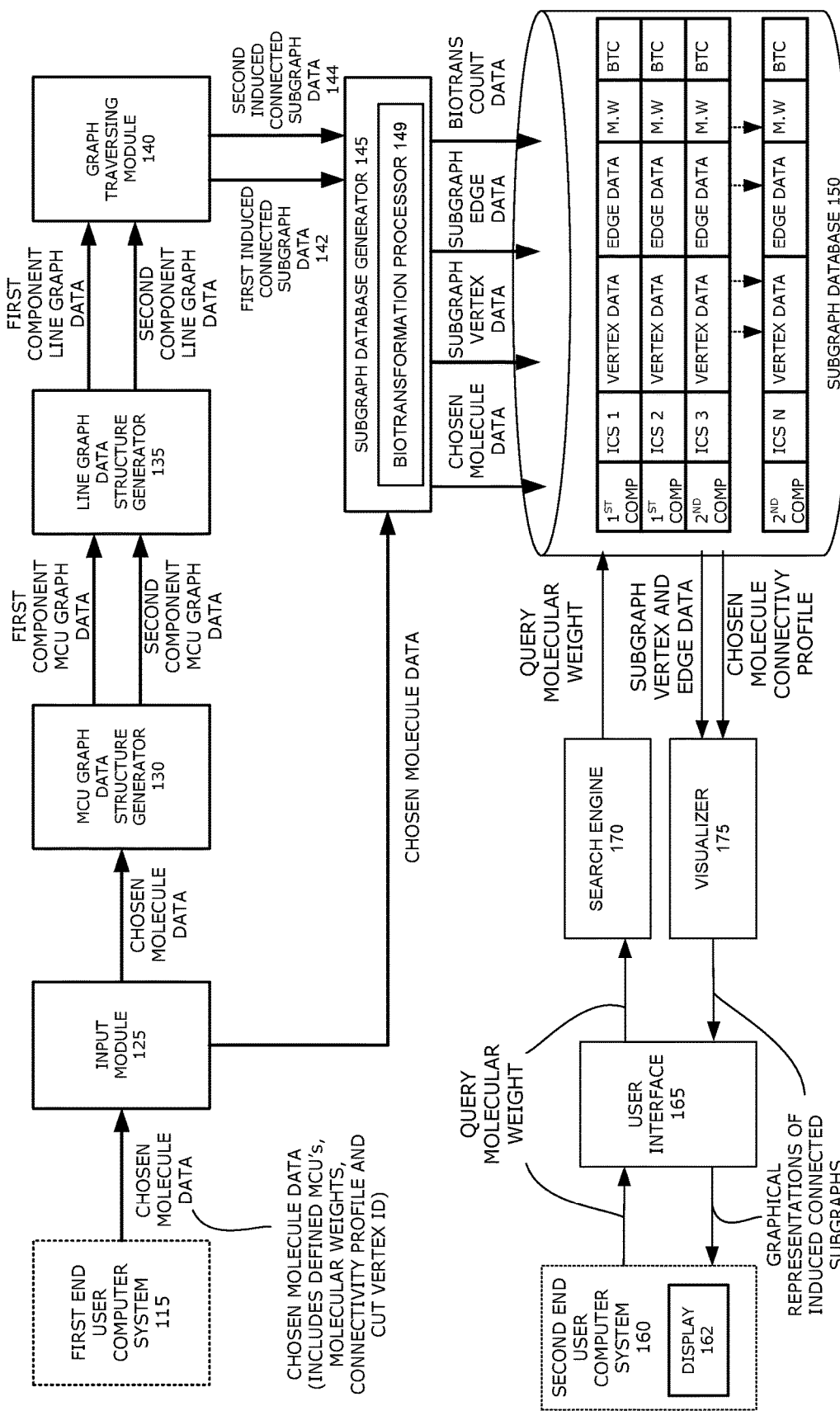
FIG. 1 shows a high-level flow diagram illustrating, by way of example, the flow of data in an embodiment of the present invention.

The cut vertex method described herein reduces the problem of bogging down a computer with complex structures and facilitates identifying large numbers of metabolites by analyzing and identifying the substructures found in two discrete subsections of a line graph representing the chosen molecule separately, and then aggregating the results of the two analyses, instead of attempting to analyze and identify all of the substructures in the entire molecule all at once, thereby facilitating drug development and design for large complex molecules. It is noted, however, that embodiments of the current invention are applicable and useful for identifying substructures for all types of molecules. The molecule to which the substructures belong are referred to as "the chosen molecule." The chosen molecule may be a large molecule, or macromolecule, or a small molecule. Macromolecules include, but are not limited to, amino acid based molecules, such as peptides, as well as polypeptides, antibodies, proteins, enzymes, immunoglobulins, lipids, nucleic acids, carbohydrates, oligonucleotides, polynucleotides, polysaccharides and polymers. A chosen molecule may also be a conjugated molecule and a cross-linked molecule.

As used herein, all amino acid three letter and single letter designations conform to those designations which are standard in the art, and are listed as follows:

Alanine Ala A Arginine Arg R Asparagine Asn N Aspartic acid Asp D Cysteine Cys C Glutamic acid Glu E Glutamine Gln Q Glycine Gly G Histidine His H Isoleucine Ile I Leucine Leu L Lysine Lys K Methionine Met M Phenylalanine Phe F Proline Pro P Serine Ser S Threonine Thr T Tryptophan Trp W Tyrosine Tyr Y Valine Val V Exemplary systems, apparatuses and methods of the invention combine small molecule MetID and Top Down proteomics approaches to provide a rapid and efficient way to not only identify and store the exhaustive pool of substructures, such as metabolites, of a given molecule, but to also provide structural characterization of the identified metabolites and visualization of the chemical structure or makeup of the metabolites. Exemplary systems, apparatuses and methods of the invention improve the operation of a conventional computer system by significantly improving search times required for the computer system to identify and characterize substructures and other metabolites of complex molecules. Computer systems configured to operate according to embodiments of the present invention can identify and characterize hundreds of millions of substructures, or even billions of substructures, in a matter of hours, as compared to conventional computerized systems and methods, which would take weeks or months to complete. The substructures may be stored in an electronic medium, such as a computer memory, displayed on a monitor or display screen associated with the computer system, printed out on a printing device associated with the computer system, or transmitted to another computer system or network for further analysis. The significantly improved processing times enabled by the present invention will play a valuable role in advancing the art of drug design and development.

The systems, apparatuses and methods of the present invention are useful for identifying metabolites and other substructures of a chosen molecule. For example, to characterize an intact protein, gas fragmentation techniques are often carried out to obtain fragment ions of the precursor protein ion. Each fragment ion may be viewed as a substructure of the precursor ion. In order to correctly characterize the structure of the precursor protein ion, the structure of each fragment ion needs to be correctly assigned based on its mass or molecular weight value. The systems, apparatuses and methods of the present invention may be applied to build the relationship between mass values of the fragment ions and their structures in the gas phase.

FIG. 1 shows a high-level flow diagram illustrating, by way of example, the flow of data in one embodiment of the present invention. As shown in FIG. 1, a first user uses a first end user computer system 115 and an input module 125 to supply chosen molecule data to the system, the chose molecule data including a set of defined MCUs for the chosen molecule, molecular weights for the MCUs and a connectivity profile for the chosen molecule. The connectivity profile indicates relative positions of minimum cleavable units and bonds, and any connections between the MCUs and bonds in the chosen molecule. The chosen molecule data also includes sufficient information to identify a cut vertex for the chosen molecule, wherein if the cut vertex is removed from a line graph representing the chosen molecule, the removal of the cut vertex would split the line graph for the chosen molecule into a first component and a second component. An MCU graph data structure generator 130 creates and populates an MCU graph data structure with data representing an MCU graph for the chosen molecule. The MCU graph data structure generator 130 stores the MCU graph data in a secondary memory device (not shown in FIG. 1) associated with the system.

A line graph data structure generator 135 retrieves the MCU graph data for the first component from the MCU graph data structure and uses it, along with the cut vertex information, to create and populate a first line graph data structure containing data representing a first line graph of the first component of the chosen molecule. The line graph data structure generator 135 also retrieves the MCU graph data for the second component from the MCU graph data structure and uses it, along with the cut vertex information, to create and populate a second line graph data structure containing data representing a second line graph for the second component of the chosen molecule. The cut vertex is the boundary between the first component and the second component of the chosen molecule.

Figure 5:
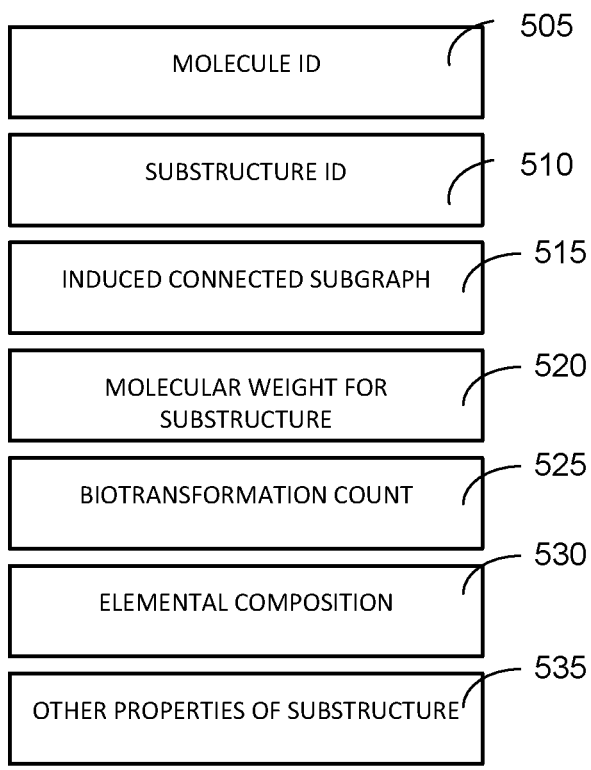
FIG. 5 shows an exemplary induced connected subgraph (ICS) record that may be stored in the ICS database in accordance with embodiments of the present invention.

A graph traversing module 140 then uses a suitable graph traversal algorithm to traverse the data in the first line graph data structure to produce and store in memory first induced connected subgraph data 142, representing all of the first induced connected subgraphs that can be derived from the first line graph represented by the first line graph data in the first line graph data structure. The graph traversing module 140 also uses the graph traversal algorithm to traverse the data in the second line graph data structure to produce and store in memory second induced connected subgraph data 144, representing all of the second induced connected subgraphs that can be derived from the second line graph represented by the second line graph data in the second line graph data structure. A subgraph database generator 145 retrieves the first induced connected subgraph data 142, the second induced connect subgraph data 144, and the chosen molecule data (particularly the molecular weights) to build and populate a first subgraph database 150 comprising a plurality of induced connected subgraph (ICS) records, each ICS record comprising at least a vertex data field populated with vertex data for the induced connected subgraph, an edge data field populated with edge data for the induced connected subgraph, a molecular weight field populated with the molecular weight for the induced connected subgraph, and a biotransformation count field populated with values representing the number biotransformations (defined below) required to transform the chosen molecule into the substructure represented by the values stored in the vertex, edge and molecular weight fields in each ICS record. The subgraph database generator 145 calculates the molecular weight for each induced connected subgraph based on the molecular weights for the MCUs in the chosen molecule data supplied by the end user. As shown in FIG. 1, the biotransformation counts may be calculated by a biotransformation processor 149 associated with the subgraph database generator 145, the biotransformation processor 149 being configured to carry out a biotransformation counting algorithm such as the algorithm depicted in FIG. 3 and described in more detail below. FIG. 5 shows an exemplary induced connected subgraph (ICS) record that may be stored in the subgraph database 150 in accordance with embodiments of the present invention.

After the subgraph database 150 is built and stored in secondary memory (and it may contain millions of records), a second user can use a second end user computer system 160 and a user interface 165 to search the subgraph databases 150 based on a given query molecular weight (or a given range of molecular weights). The query molecular weight (or range of weights) is passed to a search engine 170, which causes the system to retrieve from the subgraph database 150 vertex data and edge data for all of the records that have molecular weights that are equivalent to the query molecular weight or fall within the specified range of molecular weights. The search engine 170 also operates, in accordance with the algorithm shown in FIG. 16, explained in detail below, to calculate a modified query molecular weight and an adjusted query molecular weight, and to run a binary search on the subgraph database 150 in order to identify and retrieve the vertex data and the edge data of every ICS that straddles the cut vertex for the chosen molecule. A visualizer 175 uses the vertex data and edge data to generate a graphical representation of the induced connected subgraphs found in the search, and the graphical representation is transmitted via the user interface 165 to a display device 162 operated by the second user. In preferred embodiments, if there are two or more induced connected subgraphs that match the query mass (or range), the visualizer 175 and user interface 165 operate to rank the matching induced connected subgraphs according to the values in their respective biotransformation fields, and to display the matching induced connected subgraphs in rank order. It is noted that the first end user computer system and the second end user computer system may, in some embodiments, comprise the same computer system, and the first end user and the second end user may be the same user. In other words, the system may be configured so that the same computer system is used to initiate both the subgraph database generation and the subgraph database searching functions of the system.

Figure 2:
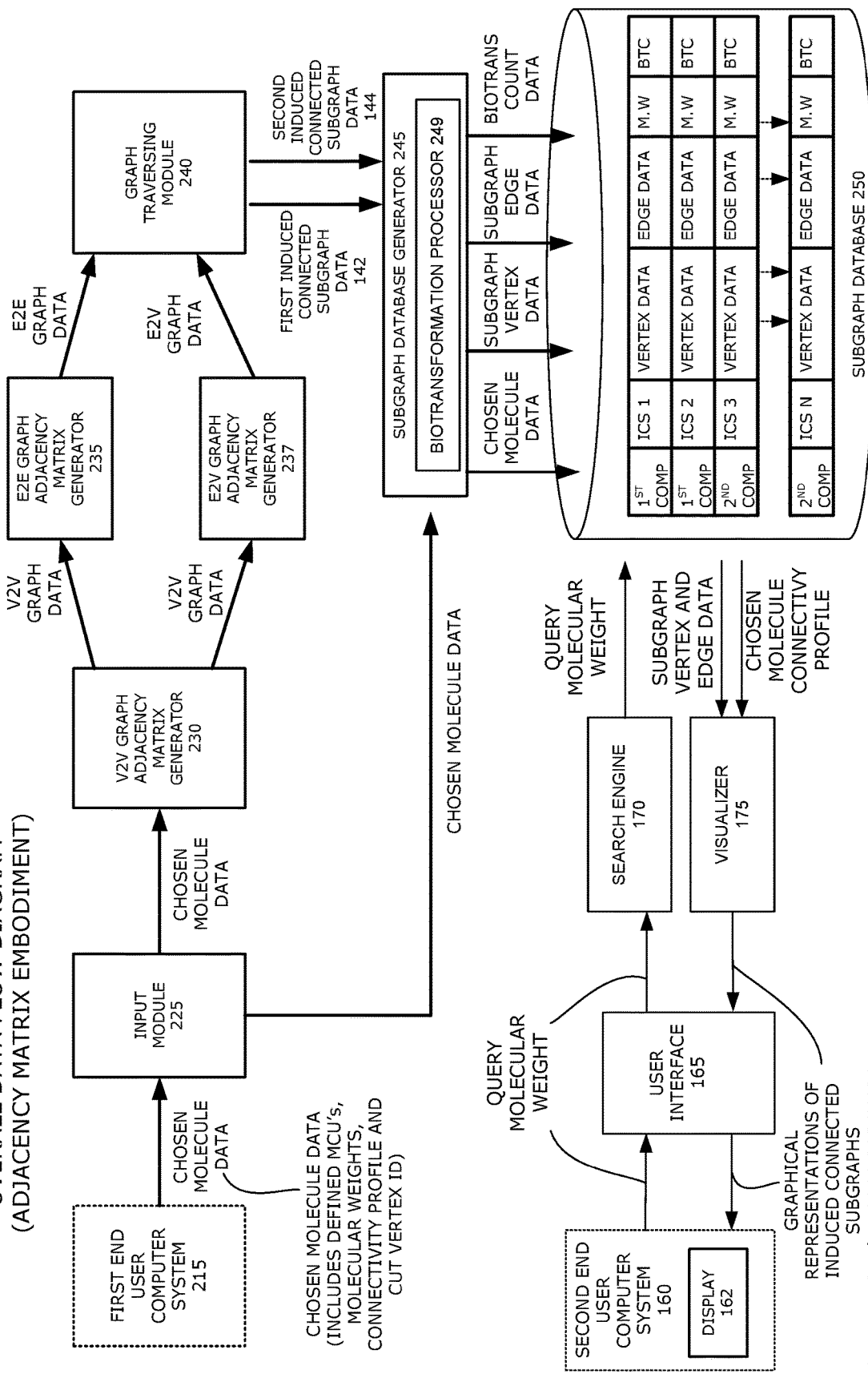
FIG. 2 shows a high-level overall flow diagram illustrating, by way of example, the flow of data in another embodiment of the present invention, wherein the data structures representing the various types of graphs are adjacency matrices.

FIG. 2 shows a high-level overall flow diagram illustrating, by way of example, the flow of data in another embodiment of the present invention, wherein the data structures representing the various types of graphs are adjacency matrices. As shown in FIG. 2, the overall data flow is substantially the same as the overall data flow in the system illustrated in FIG. 1, except that a vertex to vertex (V2V) adjacency matrix generator module 230 uses the chosen molecule data to generate and store V2V graph data, an edge-to-edge (E2E) graph adjacency matrix generator 235 uses the V2V graph data to generate and store E2E graph data, and an edge-to-vertex (E2V) graph adjacency matrix generator 237 uses the V2V graph data to generate and store E2V graph data.

Figure 3:
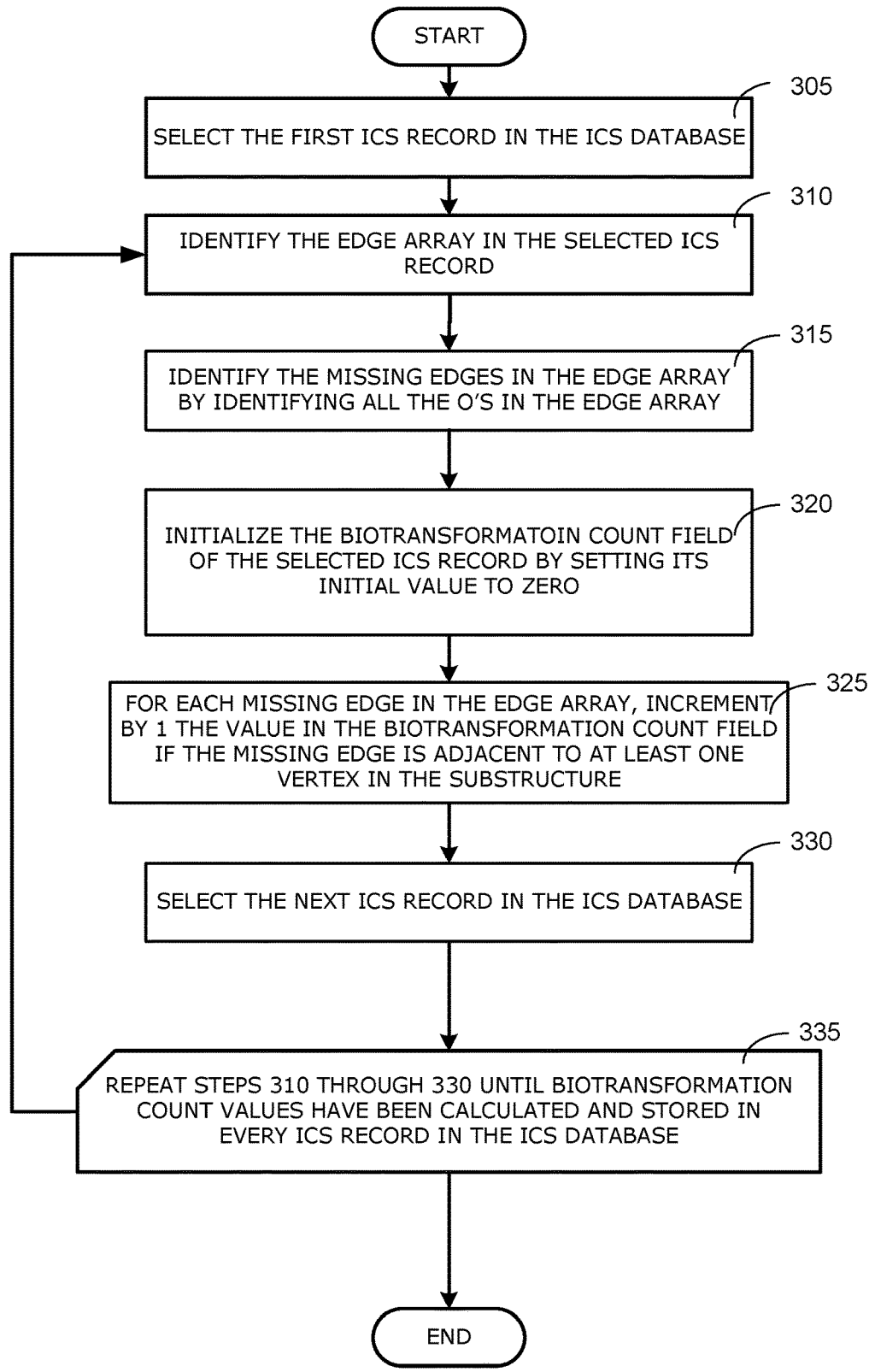
FIG. 3 shows a high-level flow diagram illustrating, by way of example, an algorithm for calculating and storing in the induced connected subgraph (ICS) database the biotransformation counts associated with each one of the induced connected subgraphs derived by embodiments of the invention.

FIG. 3 shows a high-level flow diagram illustrating, by way of example, an algorithm for calculating and storing in the ICS database the biotransformation counts associated with each one of the induced connected subgraphs represented by the vertex array data and edge array data created by the system. For the purposes of this disclosure, a "biotransformation" is defined as the breaking of a covalent bond between two MCUs.

Often, multiple metabolites will match a given query mass in a search, depending on a tolerance range specified in the search query, e.g., within ±5 ppm, within ±4 ppm, within +2 ppm, or some other limited range around the given search mass. In such cases, it is often efficient and desirable to filter (or at least prioritize) the list of metabolites returned in the search so that the metabolites that are more likely to be generated from the chosen molecule are displayed at the top of the list of metabolites returned in the search results, i.e., they are displayed before displaying the metabolites that are less likely to be generated from the chosen molecule. Because metabolites are typically produced enzymatically, and because enzymes typically hydrolyze one bond at a time, it is reasonable to assume that the metabolites that can be generated by breaking the fewest number of bonds in the chosen molecule are also the metabolites that are most likely to be generated from that chosen molecule, regardless of whether the metabolites are generated in the body or in a laboratory. A similar sequential fragmentation process occurs during gas phase fragmentation. One bond breaks at a time, with the weakest bond breaking first, followed by the breaking of the next weakest bond, and so on.

Accordingly, embodiments of the present invention, and in particular, the subgraph database generator, may include a biotransformation processor (such as a set of computer program instructions) configured to count and store in the ICS database, for each induced connected subgraph (i.e., each metabolite) represented in the ICS database, the number of biotransformations (or broken covalent bonds) that are required to transform the chosen molecule into that particular metabolite. In addition, the search engine is suitably configured to use the stored biotransformation counts, along with the query mass, to retrieve and display the metabolites in the search results in ranked order, wherein the metabolites having the lower biotransformation count values are ranked higher than the metabolites having the highest biotransformation count values. In some embodiments, the system may also be configured to filter the search results so that those metabolites requiring more than a specified maximum number of biotransformations will be filtered out of the search results and not presented on the user's display device.

Say, for example, that the chosen molecule is the linear peptide A-N-T-G-F-A-N-G-G, and one of the metabolites matching the query mass is A-N-T-G-F, and another one of the metabolites matching the query mass is T-G-F-A-N. Evidently, it takes a single broken bond to obtain the A-N-T-G-F metabolite from the chosen molecule, while it takes two broken bonds to obtain the T-G-F-A-N metabolite. In this situation, the user interface for the search query module would rank the A-N-T-G-F metabolite higher than the T-G-F-A-N metabolite.

Embodiments of the present invention are configured to produce an ICS database comprising an ICS record representing every substructure that can be generated from the chosen molecule. Each ICS record comprises at least a vertex array, an edge array and a biotransformation count field. Accordingly, as shown in FIG. 3, one algorithm for counting and storing the number of biotransformations for each substructure represented in the ICS database would proceed as follows:

Step 305—select the first ICS record in the ICS database;

Step 310—identify the edge array in the selected ICS record;

Step 315—identify the missing edges by identifying all of the 0's in the edge array;

Step 320—initialize the biotransformation count field of the selected ICS record by setting its initial value to zero;

Step 325—for each missing edge in the edge array, increment by 1 the value in the biotransformation count field if the missing edge is adjacent to at least one vertex in the substructure;

Step 330—select the next ICS record in the ICS database; and

Step 335—Repeat steps 310 through 330 above until biotransformation count values have been calculated and stored in every ICS record in the ICS database.

As discussed herein, there will be some cases in which the structure of the chosen molecule comprises two monomers (monomer A and monomer B) separated by a cut vertex. For a substructure or metabolite of such a chosen molecule that straddles the cut vertex, the number of biotransformations is the sum of the number of biotransformations needed to transform the chosen molecule into monomer A and the number of biotransformations needed to transform the chosen molecule into monomer B.

The values stored in the biotransformation count fields in accordance with this algorithm may then be used by embodiments of the invention to rank and/or filter the search results so that the substructures that are the most likely to be generated are the only substructures listed or displayed to the end user, or so that the substructures that are the most likely to be generated are listed or displayed at the top of list (i.e., before the substructures that are less likely to be generated).

Figure 4:
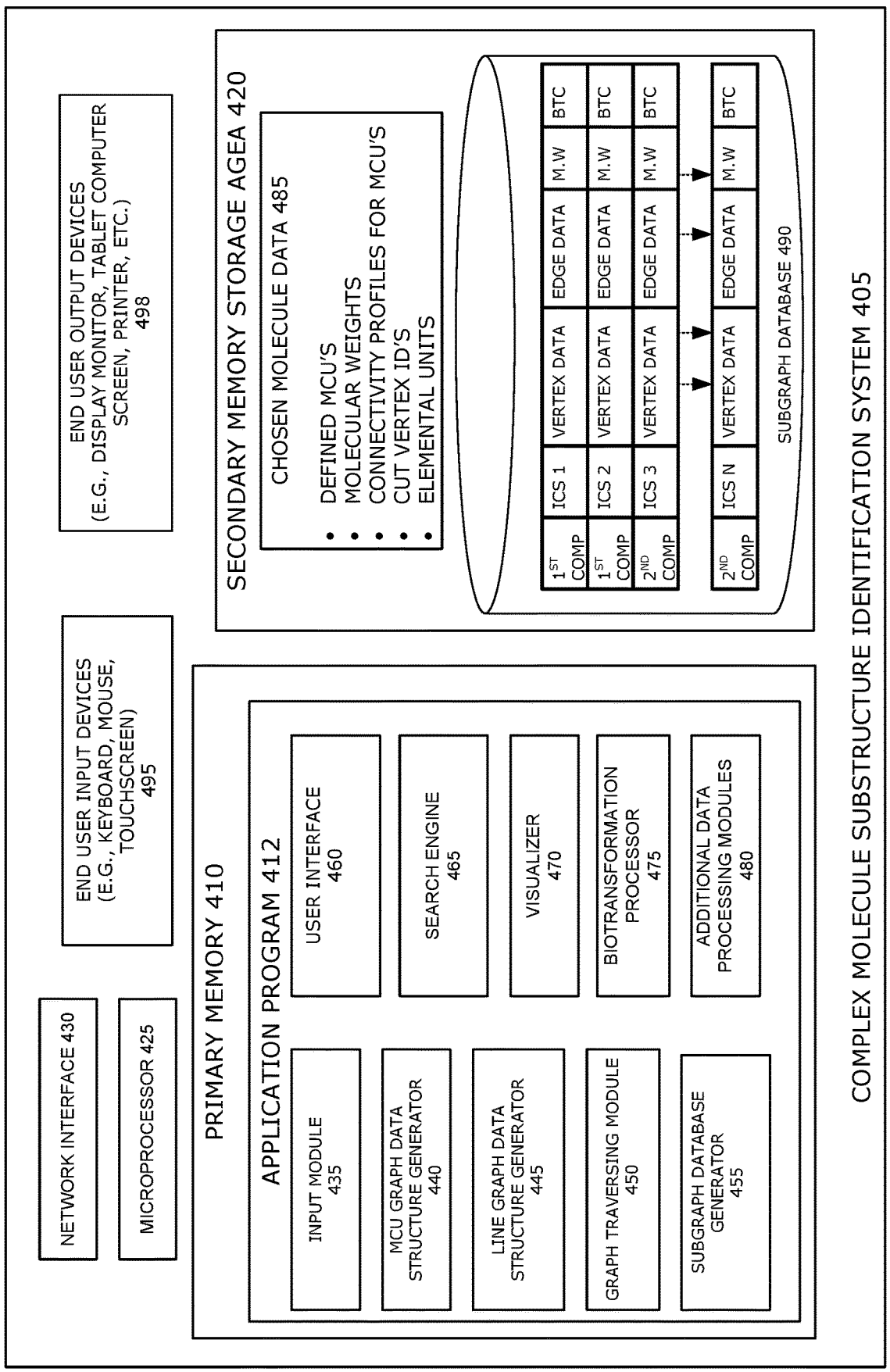
FIG. 4 shows a high-level block diagram illustrating an example of the architecture for a complex molecule substructure identification system configured to operate in accordance with an exemplary embodiment of the present invention.

FIG. 4 shows a high-level block diagram illustrating by way of example an architecture for a complex molecule substructure identification system 405 configured to operate in accordance with an exemplary embodiment of the present invention. The complex molecule substructure identification system 405 may be implemented on a general purpose or a specialized computer system, including, for example, a personal computer system, a notebook computer, a laptop, tablet or handheld computer system, an Internet-enabled smart phone or personal digital assistant computing device, or any combination of one or more thereof. Typically, the complex molecule substructure identification system 405 includes a central processing unit (CPU) or microprocessor 425, a primary memory 410 (also called random access memory (or RAM)), and a non-volatile secondary memory storage area 420 (e.g., a hard drive, a flash drive, or a CD-ROM drive). As shown in FIG. 4, the complex molecule substructure identification system 405 may also include a network interface 430, such as, for example, a wired Ethernet local area network adaptor, an 802.11 a/g/n WiFi adaptor, a universal serial bus (USB) adaptor, and/or a Bluetooth wireless data communications adaptor, to provide data communication with other computer systems, peripherals such as printers, and/or data communications networks. Program code, such as the code comprising an application program 412, and program data, such as chosen molecule data 485, can be loaded into the primary memory 410 (i.e., loaded into RAM) from the non-volatile secondary storage area 420 and provided to the microprocessor 425 for execution. Operating under the control of the application program 412, the microprocessor 425 can generate and store results in the secondary memory storage area 420 for subsequent access, display, output and/or transmission to other computer systems, other computer programs and/or other data communication networks.

The results of the substructure identification processes carried out by the microprocessor 425 under the control of the software modules in the application program 412 are stored in the secondary memory storage area 420, so that it can be viewed, navigated and modified, as required, by a human user interacting with the complex molecule substructure identification system 405 via one or more end user input devices 495 (e.g., a keyboard, mouse, stylus, touchscreen, etc.) and one or more end user output devices 498 (e.g., a display device, a printer, a tablet display screen, or smartphone display screen, etc.) operating under the control of a user interface module 460 in the application program 412. The secondary memory storage area 420, and the data it contains, may be integrated into the same physical machine as the microprocessor 425, the primary memory 410, the application program 412 and the software modules 435, 440, 445, 450, 455, 460, 465, 470, 475 and 480, as shown in FIG. 4. However, some or all of data and/or databases shown in the secondary memory storage area 420 may also reside on separate computer systems in a distributed arrangement without departing from the scope of the claimed invention.

The network interface 430 may be employed to establish a connection to remote servers and machines (e.g., mass spectrometer devices) containing or generating additional input data (not shown in FIG. 4) to be processed and a multiplicity of electronic files and documents deemed useful or necessary for carrying out the processes. The network interface 430 may also provide connectivity to remote terminals and remote computer systems (not shown) operated by other human users who wish to access and use the complex molecule substructure identification system 405 of the present invention.

The primary memory 410 may comprise without limitation one or more local or remote, fixed or removable, permanent or temporary, magnetic or optical, random access memory (RAM) areas, cache memory areas, or disk drives, contains a plurality of program modules for controlling the functions of microprocessor 425 to perform the methods of identifying substructures of complex molecules as described herein. Each one of these modules may comprise a computer software program, procedure, or process written as source code in a conventional programming language, and can be presented for execution by the microprocessor 425. The various implementations of the source code and object and byte codes can be stored on a computer-readable storage medium (such as a DVD, CDROM, floppy disk or memory card) or embodied on a transmission medium or carrier wave.

The application program 412 comprises a collection of computer software program modules 435, 440, 445, 450, 455, 460, 465, 470, 475 and 480, discussed below, each containing program instructions that cause the microprocessor 425 to perform a variety of specific tasks, as necessary, to receive various types of input data (such as chosen molecule data 485), and to execute the below-described algorithms to generate, store, transmit and display the MCU graphs, line graphs, induced connected subgraphs, substructure visualizations, biotransformation data, edge data and vertex data associated with the identification processes described herein. These software modules are flexible and may be configured to receive, process and output a large variety of different types of inputs and outputs, including without limitation, chemical structure drawing files, images and other electronic documents, graphs. layouts and schemas. The purpose and function of each one of the computer software modules 435, 440, 445, 450, 455, 460, 465, 470, 475 and 480 in the application program 412 will now be described in more detail below.

The application program 412 includes an input module 435, an MCU graph data structure generator module 440, a line graph data structure generator module 445, a graph traversing module 450, a subgraph database generator module 455, a user interface module 460, a search engine module 465, a visualizer module 470, a biotransformation processor module 475 and one or more additional data processing modules 480. The input module 435 comprises program instructions that, when executed by the microprocessor 425, causes the microprocessor 425 to receive and store in the secondary memory storage area 420 chosen molecule data 485 representing (A) a set of defined minimum cleavable units for the chosen molecule, (B) a set of bonds connecting the set of defined minimum cleavable units in the chosen molecule, (C) molecular weights for each minimum cleavable unit, and (D) a connectivity profile for the chosen molecule, the connectivity profile indicating relative positions of minimum cleavable units and bonds and connections therebetween. The input module 435 may also include program instructions that, when executed by the microprocessor 425, causes the microprocessor 425 to receive, scan, parse and/or store the data represented in a chemical diagram of the chosen molecule, the diagram including annotations that identify (A) minimum cleavable units of the chosen molecule, (B) molecular weights of each minimal cleavable unit of the chosen molecule, and (C) types of bonds connecting minimum cleavable units of the chosen molecule.

The MCU graph data structure generator 440 includes program instructions that, when executed by the microprocessor 425, will cause the microprocessor 425 to create and populate an MCU graph data structure (an example of which is shown in FIG. 9D) with data representing an MCU graph for the chosen molecule. The MCU graph data structure generator 440 will typically store the MCU graph data in the secondary memory storage area 420 or some other memory storage area (not shown in FIG. 4) that is connected to or associated with the complex molecule substructure identification system 405. The line graph data structure generator 445 retrieves the MCU graph data from the MCU graph data structure and uses it to create and populate a line graph data structure, which is also stored in the secondary memory storage area 420, or some other memory storage area (not shown in FIG. 4) that is connected to or associated with the complex molecule substructure identification system 405.

The graph traversing module 450 includes program instructions that, when executed by the microprocessor 424, will cause the microprocessor 425 to execute a suitable graph traversal algorithm to traverse the data in the line graph data structure to produce induced connected subgraph data 147, which represents all of the induced connected subgraphs that can be derived from the line graph represented by the line graph data in the line graph data structure. The subgraph database generator 455 uses the induced connected subgraph data 147 and the chosen molecule data 485 (particularly the molecular weights) to build and populate the subgraph database 490 stored in the secondary memory storage area 420. As shown in FIG. 4, the subgraph database 490 includes a plurality of ICS records, each record comprising at least a vertex data field with vertex data for the induced connected subgraph, an edge data field with edge data for the induced connected subgraph, a molecular weight field populated with the molecular weight for the induced connected subgraph, and a biotransformation count field populated with values representing the number biotransformations (defined above) required to transform the chosen molecule into the substructure represented by the values stored in the vertex, edge and molecular weight fields in each ICS record. The subgraph database generator 455 calculates the molecular weight for each induced connected subgraph based on the molecular weights for the MCUs in the chosen molecule data 485 supplied by the end user. The biotransformation processor 475 determines the biotransformations for each induced connected subgraph in accordance with the algorithm illustrated in FIG. 3 and described in detail above.

After the subgraph database 490 is built by execution of the application program 412 activated by a first user, a second user (or the first user) may operate one or more of the end user input devices 495 to activate the user interface module 460 to search the subgraph database 490 based on a given query molecular weight (or a given range of molecular weights). The query molecular weight (or range of weights) is passed to the search engine 465, which causes the system to retrieve from the subgraph database 490 vertex data and edge data for all of the records that have molecular weights that are equivalent to the query molecular weight or fall within the specified range of molecular weights. Accordingly, the user interface module 460 and the search engine module 465 together comprise program instructions that, when executed by the microprocessor 425, will cause the microprocessor 425 to (i) receive the query molecular weight from the end user; (ii) search the subgraph database 490 based on the query molecular weight to identify an ICS record having a total molecular weight in the molecular weight field that matches the query molecular weight, and (iii) transmit the vertex values in the vertex data field and the edge values in the edge data field for the identified ICS record to the user interface 460 for presentation on the end user output device 498 (e.g., a display monitor) operated by the end user.

The visualizer module 470 includes program instructions that, when executed by the microprocessor 425, will cause the microprocessor 425 to use the vertex data and edge data for the identified ICS record in the subgraph database 490 to generate a graphical representation of the identified induced connected subgraph, which is transmitted via the user interface 460 to the end user output device 498 operated by the second user. In preferred embodiments, if there are two or more induced connected subgraphs that match the query mass (or range), program instructions in the visualizer module 470 and the user interface 460 operate to rank the matching induced connected subgraphs according to the values in their respective biotransformation fields, and to display the matching induced connected subgraphs in rank order on the end user output devices 498.

The additional data processing modules 480 may include, for example, a database management program (not shown) that creates, organizes and facilitates storing and retrieving ICS records to and from the subgraph database 490. Any type of database management program can be utilized, including a flat file system, hierarchical database, relational database, or distributed database, such as those provided by Oracle Corporation, of Redwood Shores, California.

In some embodiments, the complex molecule substructure identification system 405 is capable of acting as a server configured for communicating with client computing devices using a standard web browser, such as Internet Explorer, over a data communications network (not shown), which may comprise the Internet and the World Wide Web. In such embodiments, the complex molecule substructure identification system 405 may be implemented using any one of a number of available web server applications or programs, including, for example, Internet Information Services (IIS), available from Microsoft Corporation, of Redmond, Washington.

FIG. 5 shows an exemplary induced connected subgraph (ICS) record that may be stored in the ICS database in accordance with embodiments of the present invention. As shown in FIG. 5, each ICS record in the subgraph database 490 of the secondary memory storage area 420 may comprise a plurality of different data fields associated with each induced connected subgraph of the chosen molecule, including without limitation, a molecule identifier field 505 for storing a specified identifier for each induced connected subgraph, a substructure identifier field 510 to store a specified identifier for each induced connected subgraph, an induced connected subgraph field 515 (typically a set of arrays) for storing vertex data and edge data for each induced connected subgraph, a molecular weight field 520 for storing the total molecular weight of the induced connected subgraph, a biotransformation count field 525 for storing the biotransformation count of each induced connected subgraph, an elemental composition field 530 for storing elemental composition data, and one or more other fields 535 for storing other properties associated with each one of the induced connected subgraphs.

Figure 6:
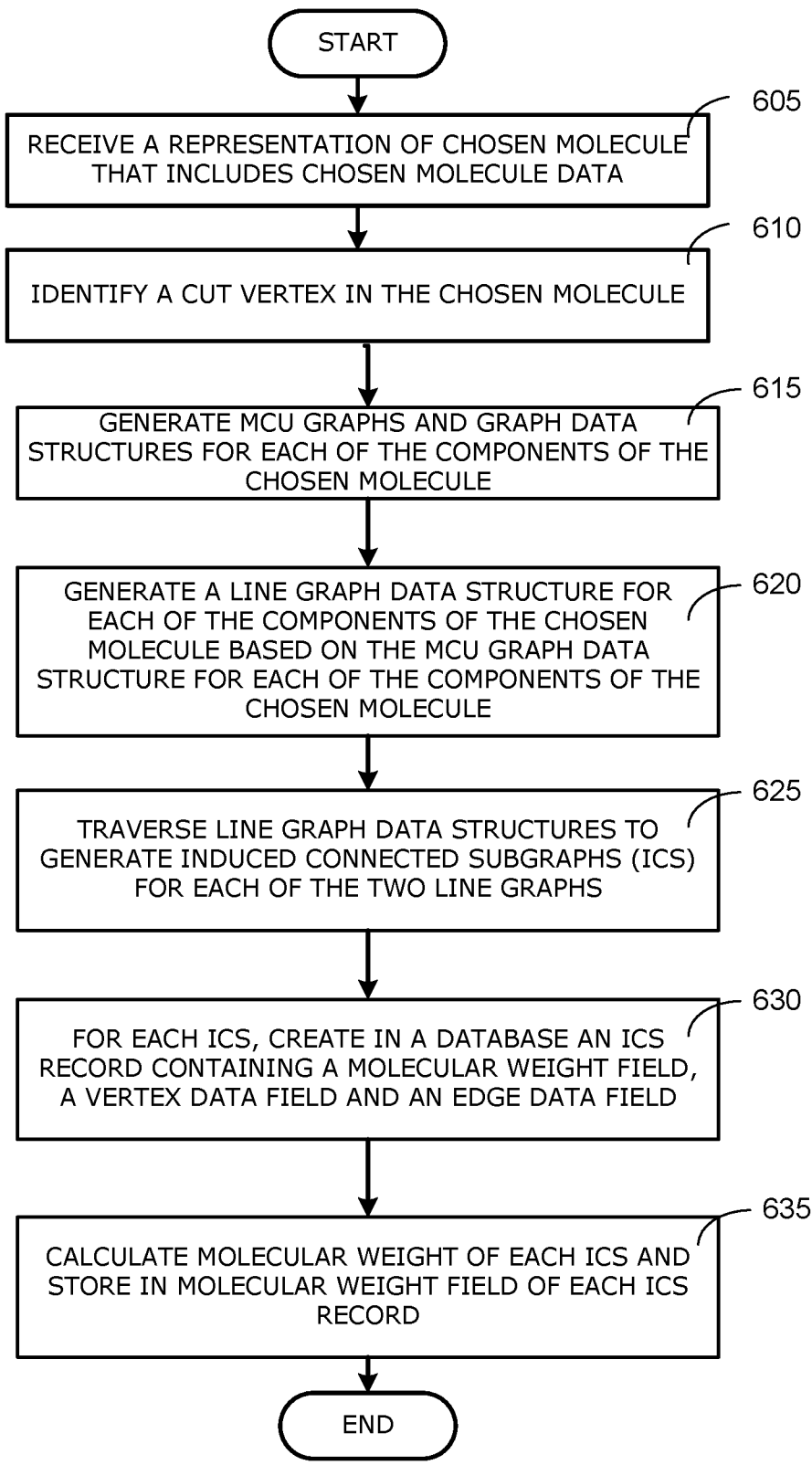
FIG. 6 is a flow diagram illustrating, in accordance with one embodiment of the present invention, the steps performed by the microprocessor to determine the full set of induced connected subgraphs and corresponding ICS records for each one of the first and second components of the chosen molecule, wherein each induced connected subgraph for a component uniquely corresponds to a chemical substructure existing entirely within that component of the chosen molecule.

FIG. 6 is representative of steps or functions of processes or computer programs that may be stored in the primary memory 410 and executed by the microprocessor 425 to perform the function of identifying metabolites of a chosen molecule.

For the purposes of this disclosure and convenience, the process illustrated in FIG. 6 may be viewed as the first phase of operation of the system of the present invention, which utilizes data structures of graphical representations of a chosen molecule in order to identify metabolites of a chosen molecule. Generally, FIG. 6 illustrates a process by which data structures are generated for the MCU graphs and the line graphs of the chosen molecule. The line graph data structures are traversed using a graph traversal algorithm in order to identify the data necessary to populate data structures of induced connected subgraphs, which represent substructures of the chosen molecule.

As the steps of the processes shown in FIG. 6 are described in this disclosure, reference will be made to FIGS. 7-15, wherein the results of the steps are shown with respect to exemplary chosen molecules.

Turning now to FIG. 6, a substructure identification process 600 of the invention includes a number of steps, the result of which provides the exhaustive set of substructures of a chosen molecule. At step 605, the system receives a representation of a chosen molecule that includes chosen molecule data. The chosen molecule data includes the minimum cleavable units in the chosen molecule, the bonds connecting minimum cleavable units in the chosen molecule, the molecular weights for each minimum cleavable unit, and the connectivity profile for the chosen molecule, the connectivity profile indicating relative positions of minimum cleavable units and bonds and connections therebetween. The representation of the chosen molecule may be in the form of an MCU graph.

In an alternative embodiment of the invention, in the first step of the process, the received representation of the chosen molecule is not an MCU graph, but rather a chemical diagram file that contains a structure, formula, drawing or other suitable representation of the chosen molecule. In this instance, the system, at step 615, generates an MCU graph and a corresponding MCU graph data structure for the chosen molecule, based upon the chemical structure of the molecule and the user-defined MCU or based upon the chosen molecule data.

Figure 7:
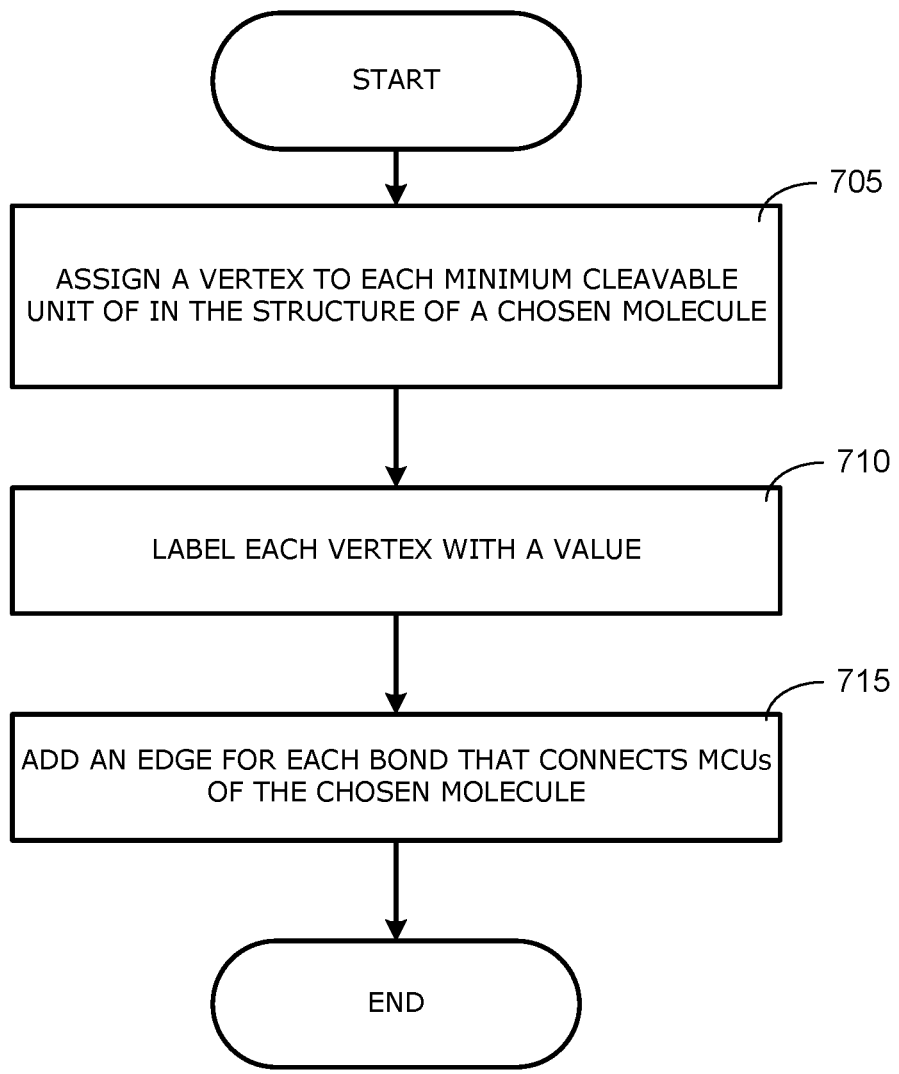
FIG. 7 is a flow diagram illustrating an algorithm for generating an MCU graph for a chosen molecule in accordance with an embodiment of the present invention.

The MCU graph adjacency matrix may be generated by matrix generator module. The MCU graph may be generated from a chemical diagram file, such as a ChemDraw file, a chemical table file, or a HELM representation (Hierarchical Editing Language for Complex Macromolecules) of the molecule. The chemical diagram file may also be generated using the simplified molecular-input line-entry system (SMILES), As shown in FIG. 7, an MCU graph of the hypothetical chosen molecule may be generated as follows: At step 705, assign a vertex to each minimum cleavable unit of the chosen molecule. At Step 710, assign an identifier or value to each vertex. The value may be a numerical value, for example. As shown in FIG. 9A, the hypothetical chosen molecule has 11 vertices. The vertices are assigned numerical values 1, 2, 3, 4, 5, 10, 11, 12, 13 and 15. One vertex is denoted by the letter "Q". At step 715, add an edge for each bond that connects the MCUs of the chosen molecule. The edges of the MCU graph for the hypothetical chosen molecule as denoted by the black lines connecting the vertices. An exemplary MCU graph is shown in FIG. 9A.

Returning to FIG. 6, at step 610, the user defines a cut vertex or cut vertex in the chosen molecule. In this instance, the cut vertex of the hypothetical molecule is designated as vertex "Q". As stated previously, a cut vertex of a connected graph is a vertex whose removal results in at least two connected components of the original graph (not counting the removed cut vertex itself). In this scenario, removal of cut vertex Q from the structure set forth in FIG. 9A, results in two subcomponents of the chosen molecule, which can conveniently be referred to as monomer A and monomer B. Monomer A is represented by vertices 1 through 5, connected by edges as depicted, and monomer B is represented by vertices 10-14, connected by edges as depicted in FIG. 9A. Separating the chosen molecule into its components or subcomponents facilitates identification of the exhaustive pool of substructures of the molecule, and is particularly useful for molecules having very high numbers of substructures.

At step 615, the system generates MCU graph data structures for each of the components of the chosen molecule, in this case for monomer A and monomer B. The MCU graph data structure that is generated by the system is preferably an adjacency matrix or an adjacency list. An exemplary MCU graph adjacency matrix for the hypothetical chosen molecule represented in FIG. 9A is set forth in FIG. 9B. The adjacency matrix of the MCU graph is a Vertex to Vertex matrix (V2V). The Vertex to Vertex matrix comprises a data structure that in an exemplary embodiment of the invention is configured as an n by n matrix for a chosen molecule of n elemental components or n minimum cleavable units. Each slot in the matrix contains a numerical value of 1 (one) if two vertices are connected to one another or are adjacent, and a 0 if there is no adjacency between the two. Both the rows are the columns of the V2V matrix for monomer A of the hypothetical chosen molecule are labelled 1 through 5 to represent the 5 vertices present in the corresponding monomer A MCU graph. By way of example, as shown in FIG. 9B, vertices 1 and 2 are adjacent, as denoted by the "1" in the row 1, column 2 of the matrix. On the other hand, vertices 1 and 5 are not adjacent, as denoted by the "0" set forth in row 1, column 5 of the matrix. Likewise, in the MCU graph for monomer B, vertices 10 and 10 are connected, as denoted by the "1" in row 10, column 11 of the monomer 1 adjacency matrix, and vertices 11 and 14 are not connected and therefore assigned a "0" in the adjacency matrix representing monomer 2.

At step 620, the system generates a line graph data structure (also known as a "bond graph data structure" or "edge graph data structure") from the MCU graph data structure. For ease of understanding, a line graphs corresponding to the monomer A and monomer B of the hypothetical chosen molecule MCU graph adjacency matrices are depicted in FIG. 9C. Generally, the line graph encoding process is such that (i) each vertex of the line graph represents a covalent bond between the between the MCUs of the chosen molecule and (ii) two vertices of the line graph are connected by an edge if and only if the corresponding covalent bonds are incident to the same MCU in the MCU graph.

Figure 8:
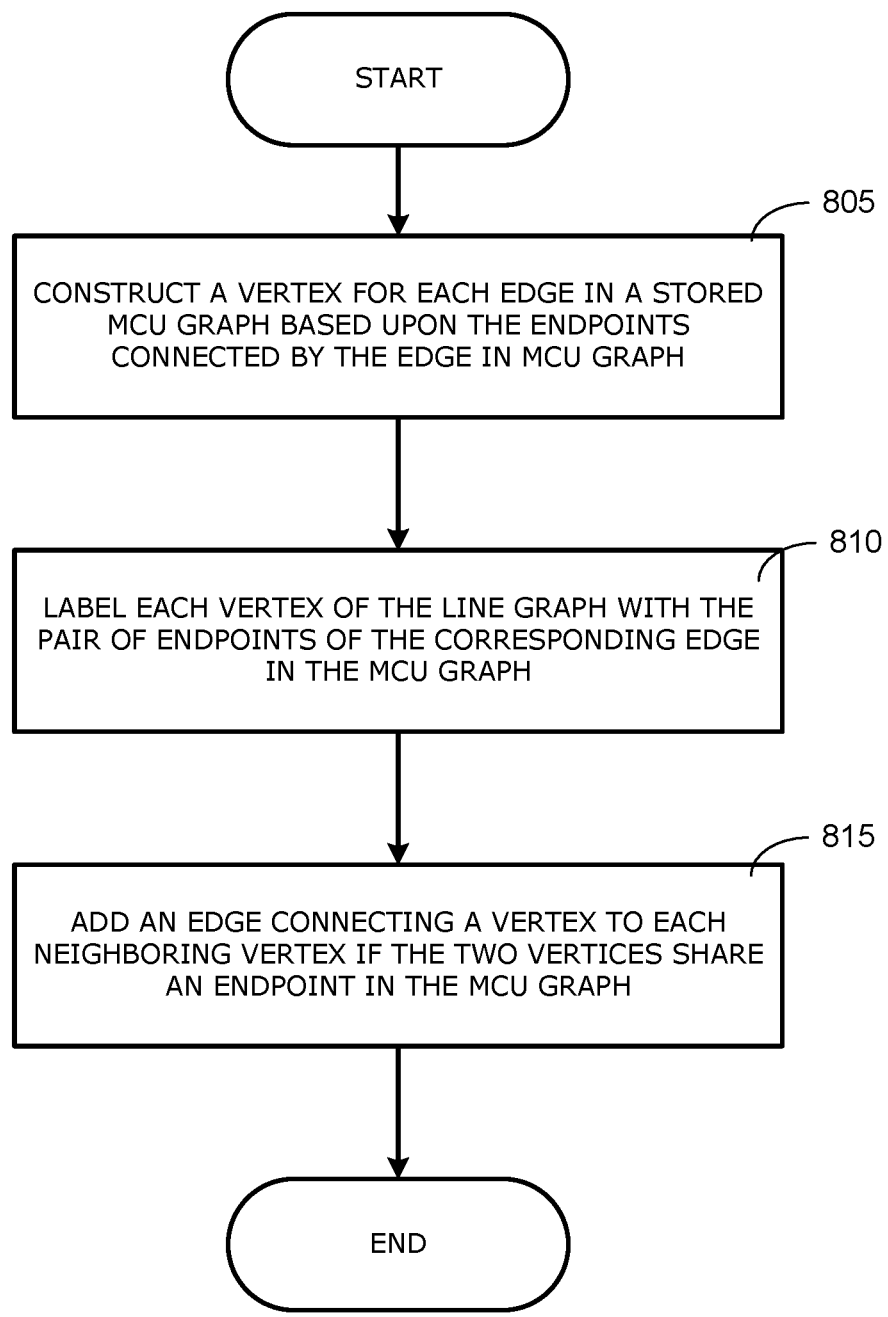
FIG. 8 is a flow diagram illustrating an algorithm for generating a line graph for an MCU graph in accordance with one embodiment of the invention.

As illustrated by the flow diagram of FIG. 8, an algorithm for generating a line graph proceeds as follows: At step 805, vertices of the line graph are constructed from edges in the MCU Graph of the chosen hypothetical molecule, based upon the endpoints connected by each edge. Each vertex of the line graph is assigned a unique index, for example a numerical value, based upon the values assigned to the vertices of the corresponding MCU graph. The vertices of line graph correspond to the edges of the MCU. For example, for the line graph of monomer A of the hypothetical chosen molecule, vertex A of FIG. 9C corresponds to the edge connecting vertices 1 and 2 of the monomer A MCU graph of FIG. 9A; vertex B corresponds to the edge connecting vertices 1 and 3 of the monomer A MCU graph of FIG. 9A; vertex C of FIG. 9C corresponds to the edge connecting vertices 1 and 4 of the monomer A MCU graph of FIG. 9A; Vertex D of FIG. 9C corresponds to the edge connecting vertices 2 and 5 of the monomer A MCU graph of FIG. 9A. Vertex E of FIG. 9C corresponds to the edge connecting vertices 4 and 3 of the monomer A MCU graph of FIG. 9A; and vertex F of FIG. 9C corresponds to the edge connecting vertices 4 and 5 of the monomer A MCU graph of FIG. 9A.

The line graph data structure generated by the system of the invention is preferably a line graph adjacency matrix or adjacency list. In one embodiment of the invention, the line graph data structure is generated automatically by computer code, such as by a line graph matrix generator module and an edge to vertex (E2V) matrix generator module.

Typically, there are two types of adjacency matrices of the line graph, namely an Edge to Edge (E2E) matrix and an Edge to Vertex (E2V) matrix. For each matrix a 0,1 notation may be used to describe a connection between components of the chosen molecule (designated "1") or the lack thereof (designated "0"). The 0,1 notation is an exemplary notation that may be used for a matrix. Any notation is suitable that permits distinguishing between the presence and the absence of a connection between components of the chosen molecule.

The Edge to Edge matrix comprises a data structure that, in an exemplary embodiment of the present invention, is configured as an n by n matrix for a chosen molecule of n elemental components or n minimum cleavable units. Each slot in the matrix contains a numerical value of 1 (one) if edge E1 and edge E2 are adjacent, and a 0 (zero) if there is no adjacency between the two.

The Edge to Vertex matrix comprises a data structure that, in an exemplary embodiment of the present invention, is configured as an n by n matrix for a chosen molecule of n elemental components or minimum cleavable units. Each slot in the matrix contains a numerical value of 1 (one) if an edge and a given vertex are adjacent, and a 0 (zero) if there is no adjacency between the two.

Exemplary line graph adjacency matrices (E2E) corresponding to the MCU graph and MCU graph data structure for monomer A and monomer B of the hypothetical chosen molecule represented in FIG. 9A are set forth in FIG. 9D.

At step 625, the system uses a graph traversing program (or subroutine) containing program instructions that, when executed by the microprocessor 425, causes the microprocessor 425 to perform the steps of a graph traversal algorithm to traverse the line graph data structures of the components of the chosen molecule, in this case the E2E and E2V matrices for monomer A and monomer B, to produce and store induced connected subgraphs of the line graphs of monomer A and monomer B.

In one embodiment of the invention, the graphical search is a depth-first search. The process proceeds as follows: First, individual vertices of the line graph data structure are added as connected components. Next, for any connected component, (i) its vertex index is defined as the minimum index of its constituent vertices; (ii) its neighboring vertices are identified; (iii) a new connected component, defined as the union of the current connected component and each one of its neighboring vertices that has an index that is above the index of the current connected component, is added to the list of connected components; and (iv) the search (traversing the line graph adjacency matrices) proceeds inductively until all connected components have been enumerated. The lack of infinite loops is guaranteed by the particular direction of the search in the direction of non-decreasing vertex indices.

As the connected components (induced connected subgraphs) are enumerated, the system, at step 630 creates and stores an induced connected subgraph record (ICS record) in a subgraph database 490 in the secondary memory storage area 420. Preferably, though not necessarily, the ICS records for each of the components of the chosen molecule are stored in different subgraph databases. For example, the ICS records for monomer A may be stored in a first subgraph database, and the ICS records for monomer 2 may be stored in a second subgraph database. Each ICS record contains a molecular weight field, a vertex data field and an edge data field. FIGS. 17A and 17B provide exemplary ICS records for monomer A of a chosen molecule that is a synthetic dimeric peptide, generated in accordance with some embodiments of the invention.

At step 635, the system calculates and stores the total molecular weight corresponding to each induced connected subgraph and stores the molecular weight in the molecular weight field of the ICS record in the ICS database. At the completion of the steps 630 and 635, all induced connected subgraphs have been enumerated and stored and the corresponding molecular masses have been calculated and are stored, preferably in one or more subgraph databases. This completes the first phase of the metabolite identification process of the invention, which may be referred to as the subgraph database building phase.

Figure 10:
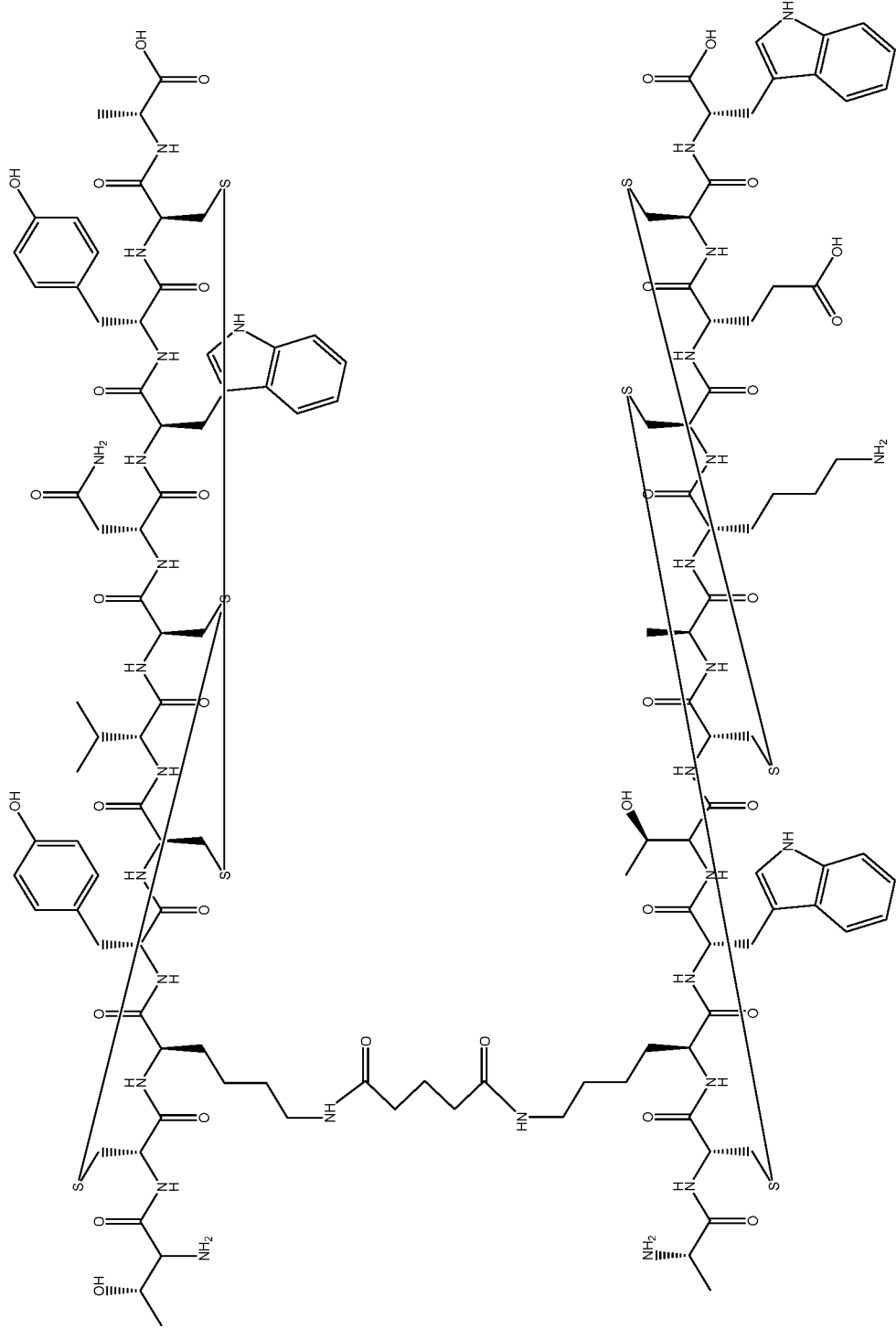
FIG. 10 shows the chemical structure of a synthetic dimer, which is one example of a large molecule that could comprise the chosen molecule in an implementation of the present invention.
Figure 11:
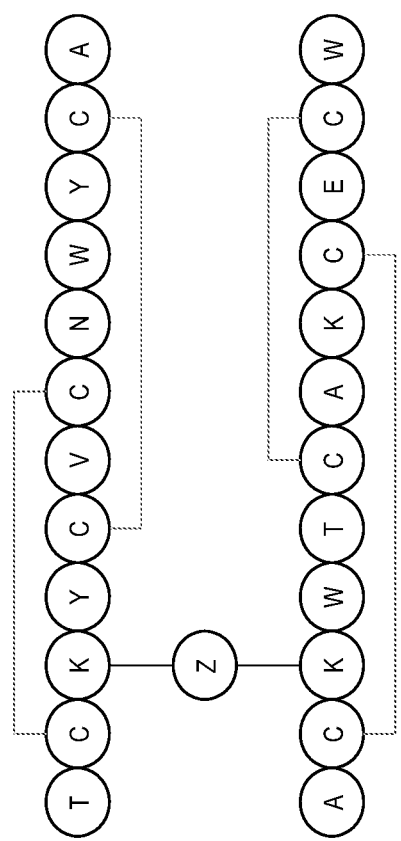
FIG. 11 shows an example of an MCU graph for the synthetic dimer molecule shown in FIG. 10.

FIG. 10 shows the chemical structure of a chosen molecule that is a heterodimeric synthetic peptide. FIG. 11 is an MCU graph that represents the chosen hetero dimeric synthetic peptide shown in FIG. 10. The vertex Z represents the selected cut vertex within the molecule. The amino acids representing other vertices are depicted by encircled single letter abbreviations. In this instance an MCU of the chosen dimeric peptide is selected as an amino acid. Thus no cleavage is permitted beyond the amino acid level. As shown in FIG. 10, there are 12 amino acids in monomer A of the chosen molecule and thus 12 vertices in the monomer A MCU graph, as represented by the encircled letters. The MCU graph contains 13 edges, depicted the connected circles and by the solid black lines connecting the vertices.

Figures 12A, 12B:
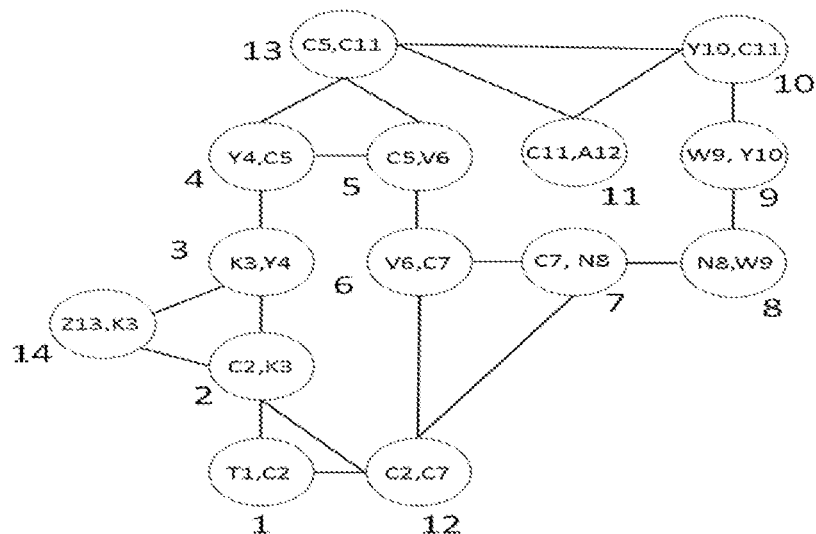
FIGS. 12A and 12B show a line graph and a line graph data structure, respectively, which may be generated, in accordance with an embodiment of the invention, to represent the first monomer of the synthetic dimer shown in FIG. 10.

FIGS. 12A and 12B show, respectively, a line graph and its corresponding adjacency matrix for monomer A of the heterodimeric synthetic peptide of FIG. 11, generated in accordance with an embodiment of the invention. Vertices of the line graph are represented as circles and numbered 1-14. For ease of understanding vertices contain the single letter amino acid and position within the peptide that represent the endpoints of a given edge of the MCU graph of monomer A.

The corresponding E2V Matrix data structure for monomer A is set forth in FIG. 14. In the E2V matrix Edges are represented as rows 1-14 and vertices are represented as columns 1-13.

Figures 14A, 14B:
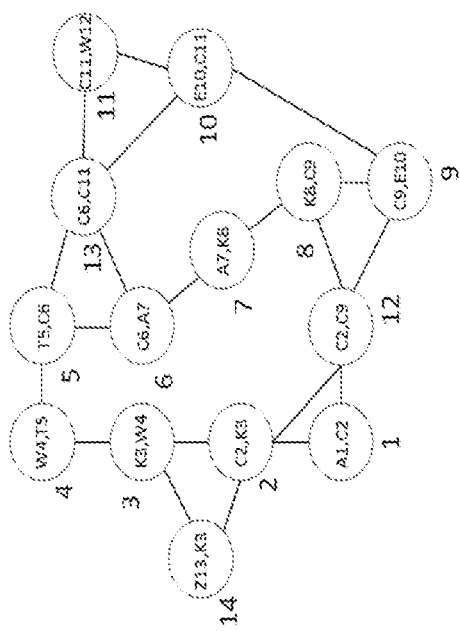
FIGS. 14A and 14B show a line graph and a line graph data structure, respectively, which may be generated, in accordance with an embodiment of the invention, to represent the second monomer of the synthetic dimer shown in FIG. 10.
Figure 15:
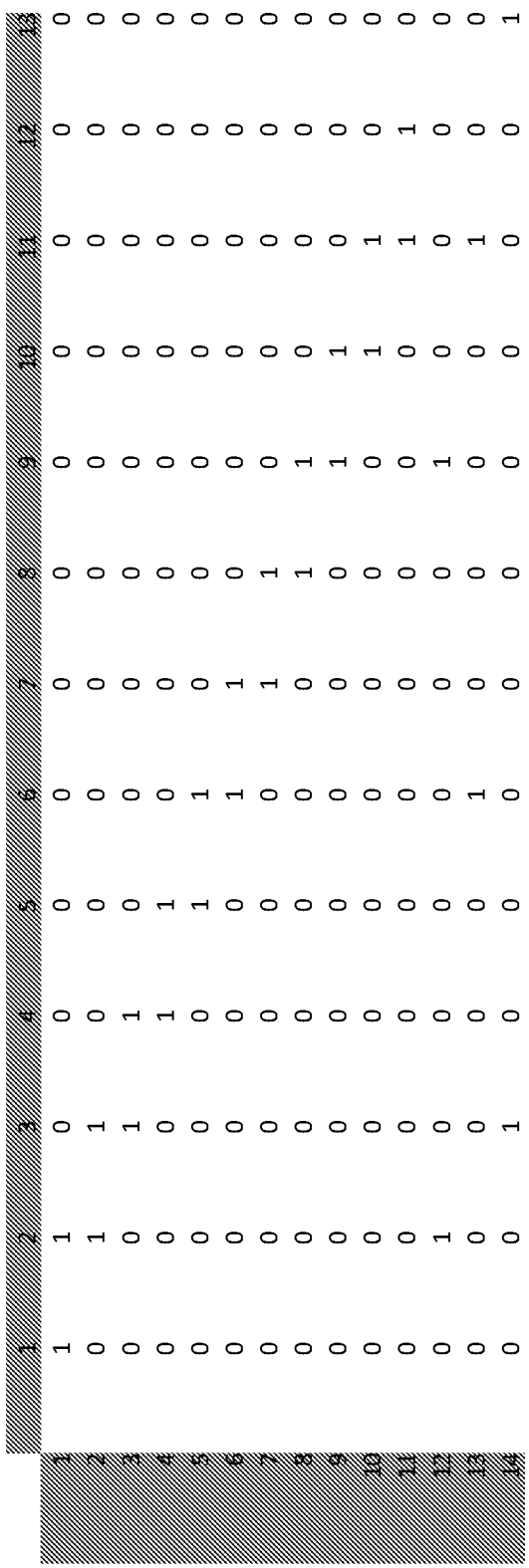
FIG. 15 shows an Edge to Vertex data structure which may be generated in accordance with an embodiment of the invention to represent the second monomer of the synthetic dimer shown in FIG. 10.

FIGS. 14A and 14B show, respectively, a line graph and its corresponding adjacency matrix for monomer B of the heterodimeric synthetic peptide of FIG. 11, generated in accordance with an embodiment of the invention. Vertices of the line graph are represented as circles and numbered 1-14. For ease of understanding vertices contain the single letter amino acid and position within the peptide that represent the endpoints of a given edge of the MCU graph of monomer A. The corresponding E2V Matrix data structure for monomer A is set forth in FIG. 15. In the E2V matrix Edges are represented as rows 1-14 and vertices are represented as columns 1-14.

FIGS. 17A and 17B show exemplary ICS records for monomer A of the chosen synthetic heterodimeric molecule, stored in a subgraph database generated in accordance with an embodiment of the invention, including the molecular weight field, vertex array field, and edge array field. The ICS records represent induced connected subgraphs of the line graph of the chosen synthetic heterodimeric peptide. As shown in rows 4 and 5 of FIG. 15, two of the ICS records show the same molecular weight, but differing vertex values in the vertex data field and differing edge values in the edge data field. The invention allows the user to distinguish ICSs (and thus substructures of the chosen molecule) that have the same molecular weight.

FIGS. 18A and 18B show exemplary ICS records for monomer B of the chosen synthetic heterodimeric molecule, stored in a subgraph database generated in accordance with an embodiment of the invention, including the molecular weight field, vertex array field, and edge array field. The ICS records represent induced connected subgraphs of the line graph of the chosen synthetic heterodimeric peptide.

Figure 16:
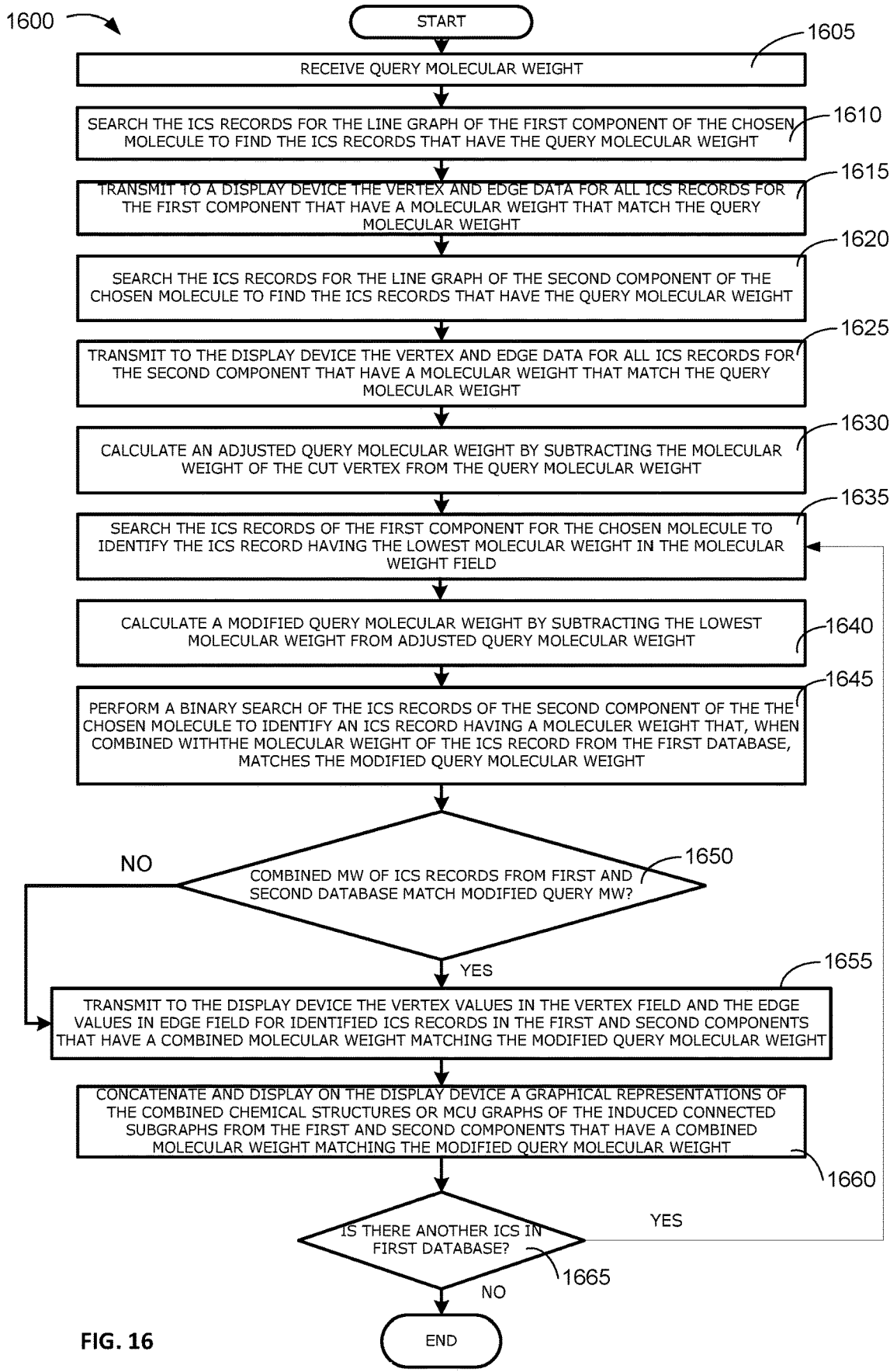
FIG. 16 is a flow diagram illustrating the steps, in accordance with one embodiment of the present invention, in searching the database of induced connected subgraphs (ICS database) to identify a substructure of a chosen molecule.
Figure 19A:
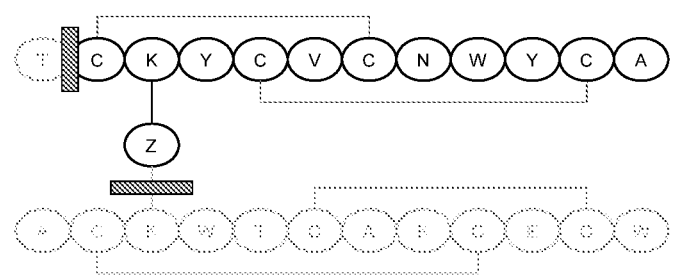
FIGS. 19A, 19B, 20A, 20B, 21A, 21B, 22A and 22B show MCU graphs and chemical structures of substructures of monomer A, generated in accordance with an embodiment of the invention, and corresponding to the subgraph database entries depicted in FIGS. 17A-17D, respectively.
Figure 19B:
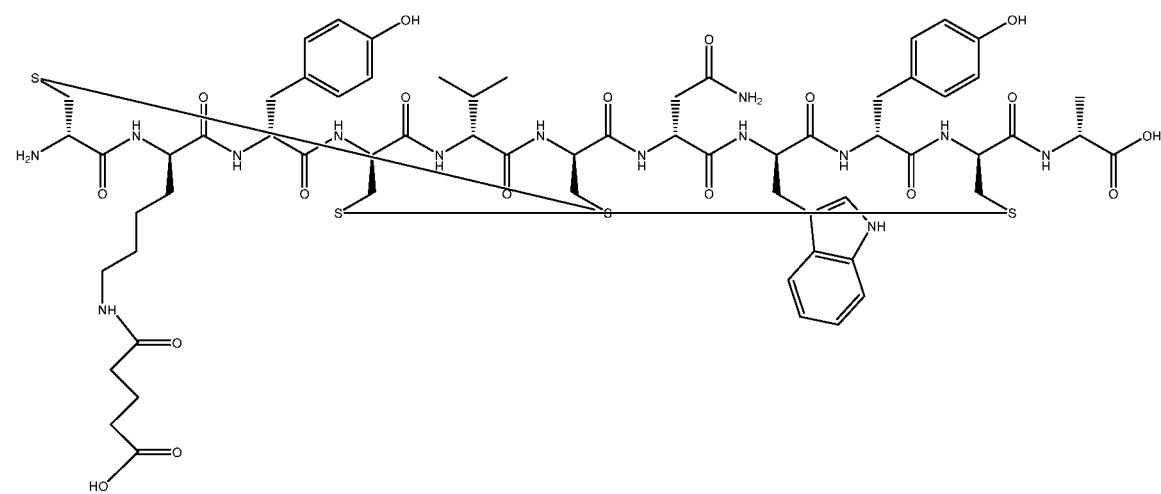
Figure 20A:
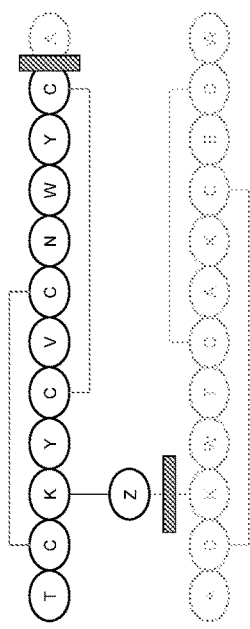
Figure 20B:
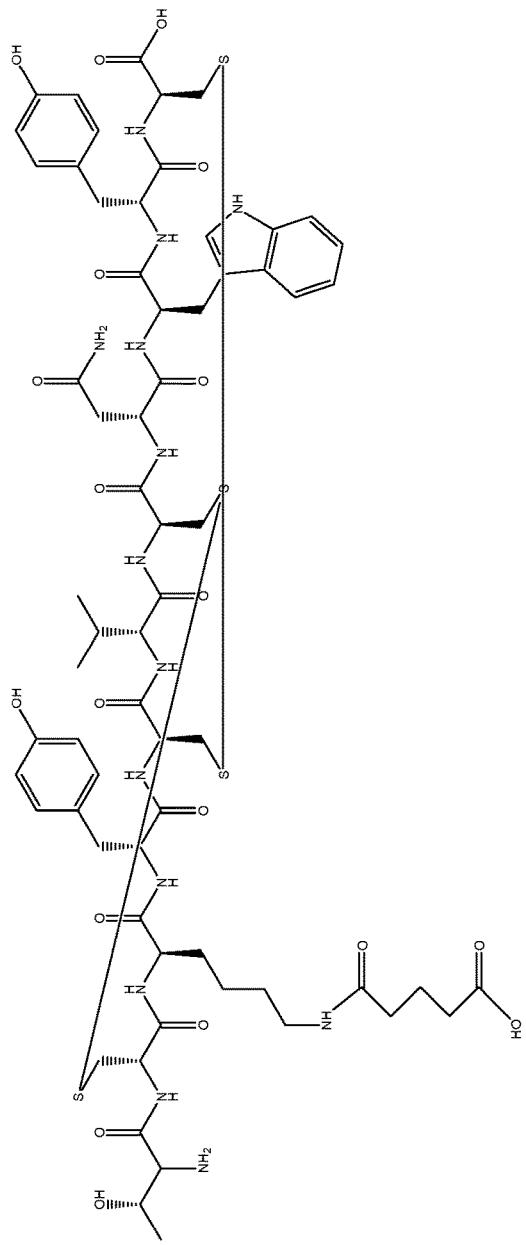
Figure 21A:
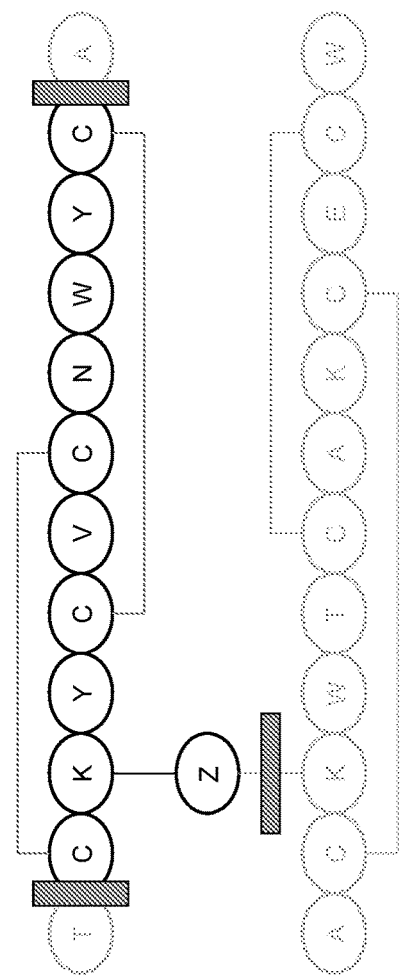
Figure 21B:
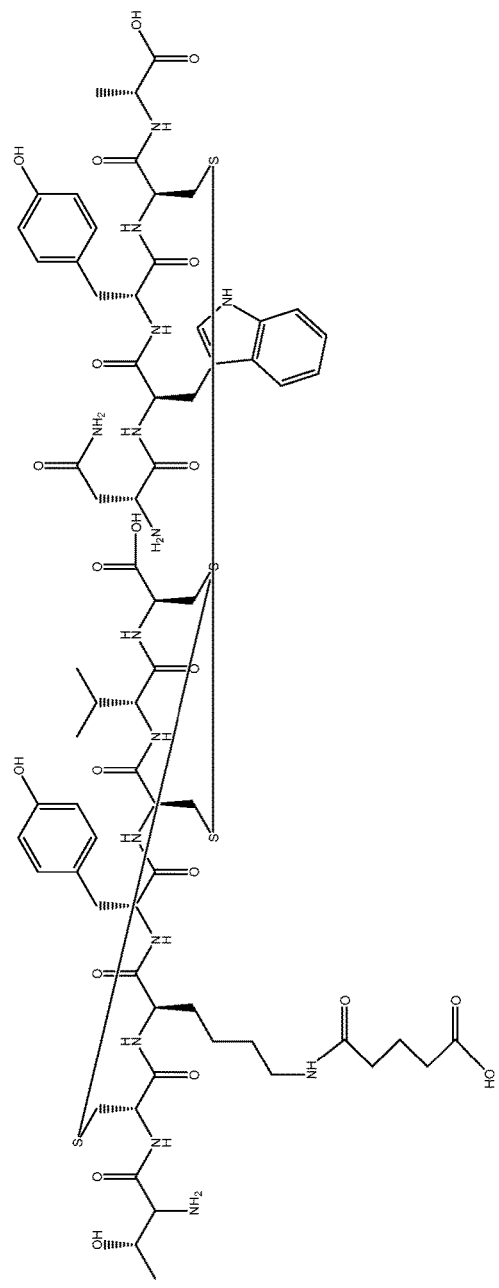
Figure 22A:
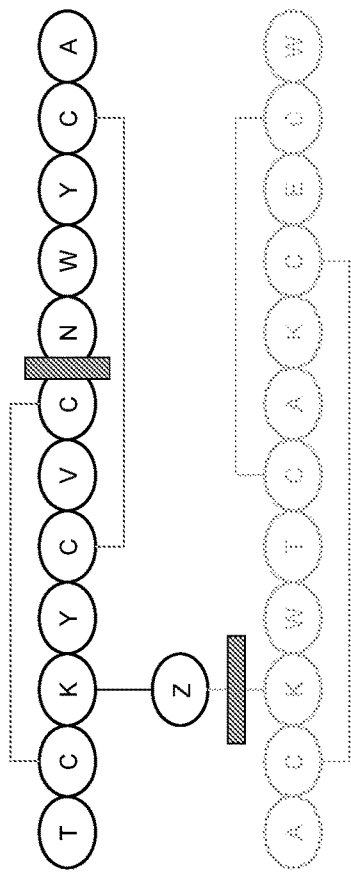
Figure 22B:
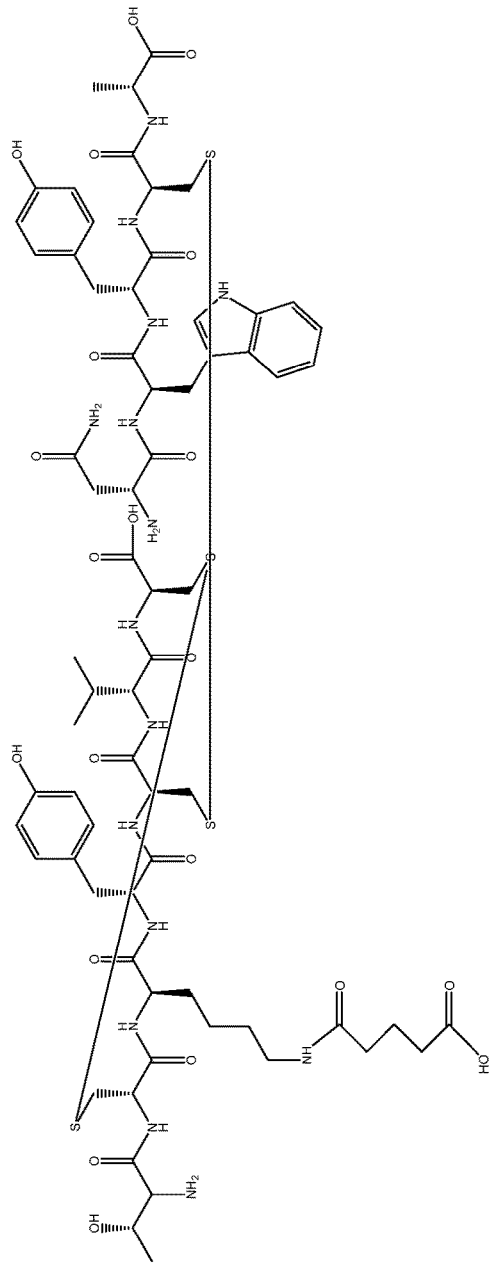
Figure 23A:
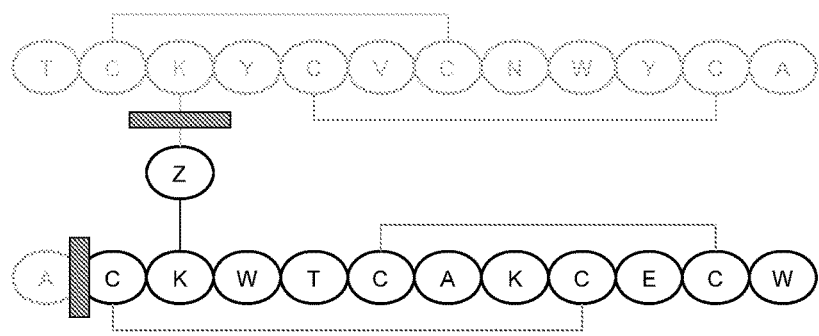
FIGS. 23A, 23B, 24A, 24B, 25A, 25B, 26A, and 26B show MCU graphs and chemical structures of substructures of monomer B, generated in accordance with an embodiment of the invention, and corresponding to the subgraph database entries depicted in FIGS. 18A-18D, respectively.
Figure 23B:
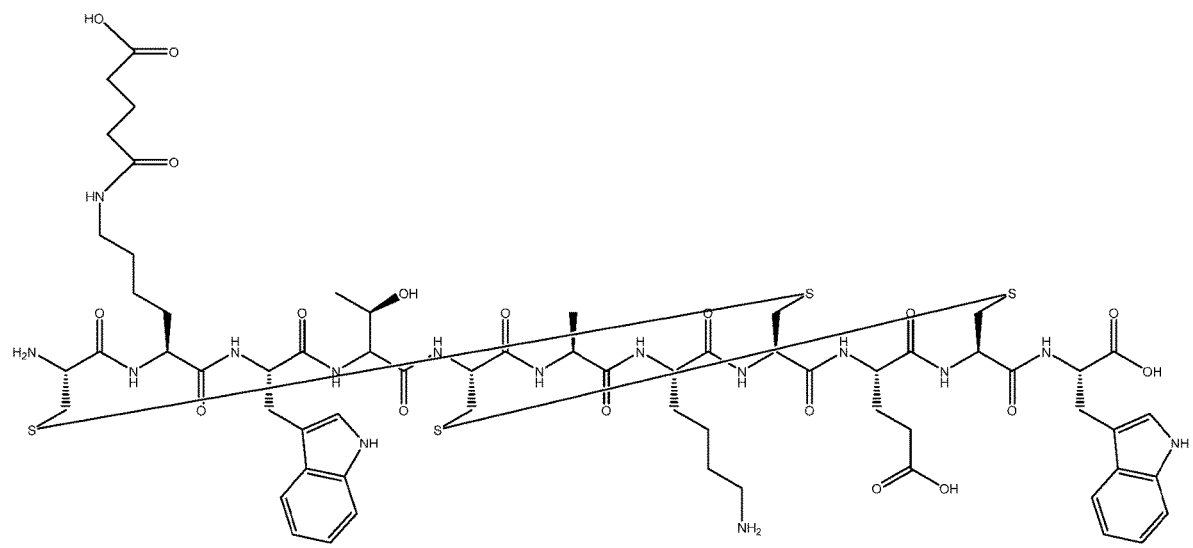
Figure 24A:
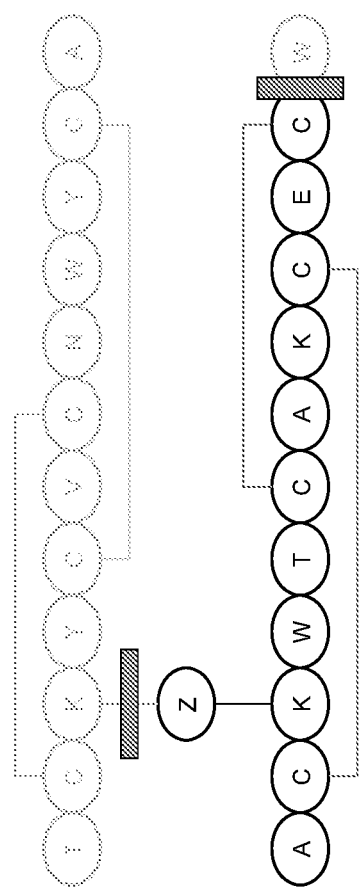
Figure 24B:
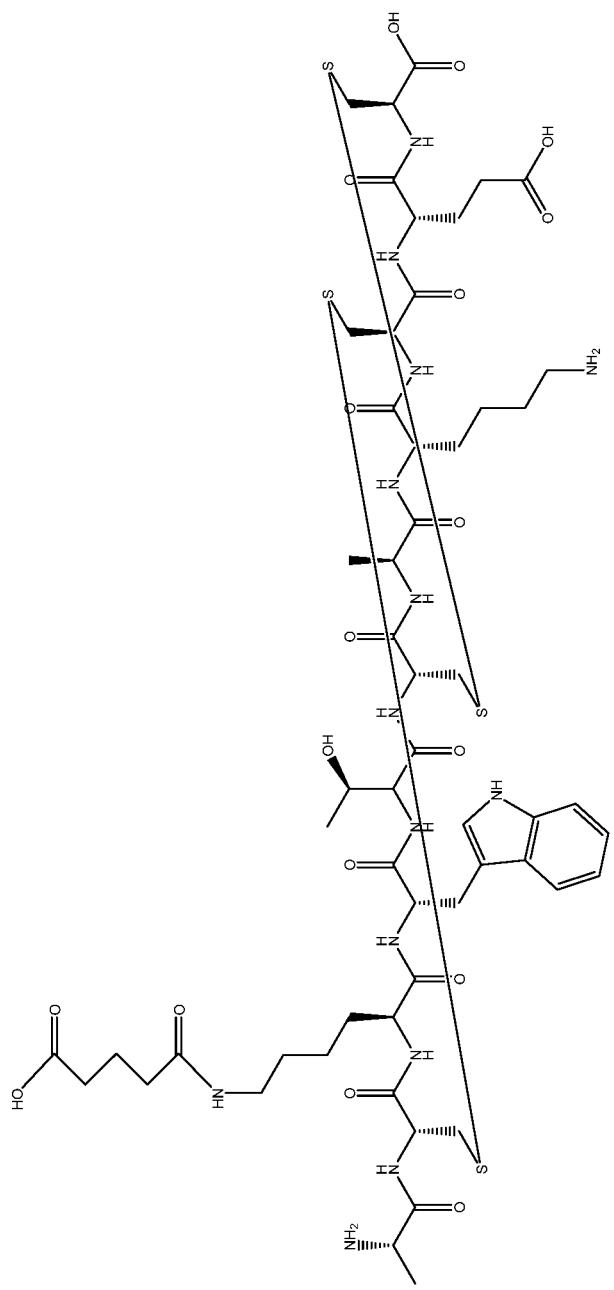
Figure 25A:
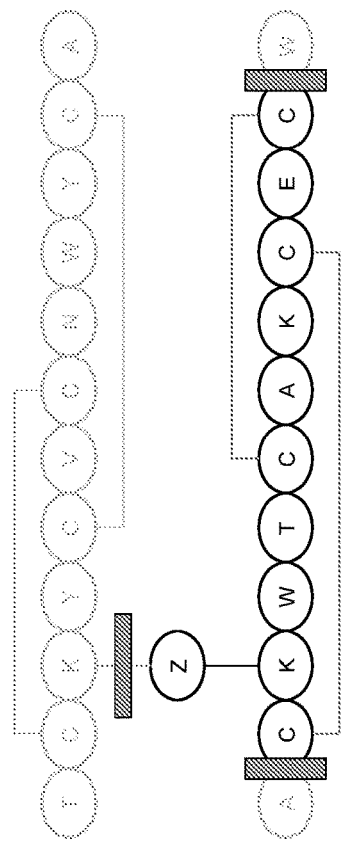
Figure 25B:
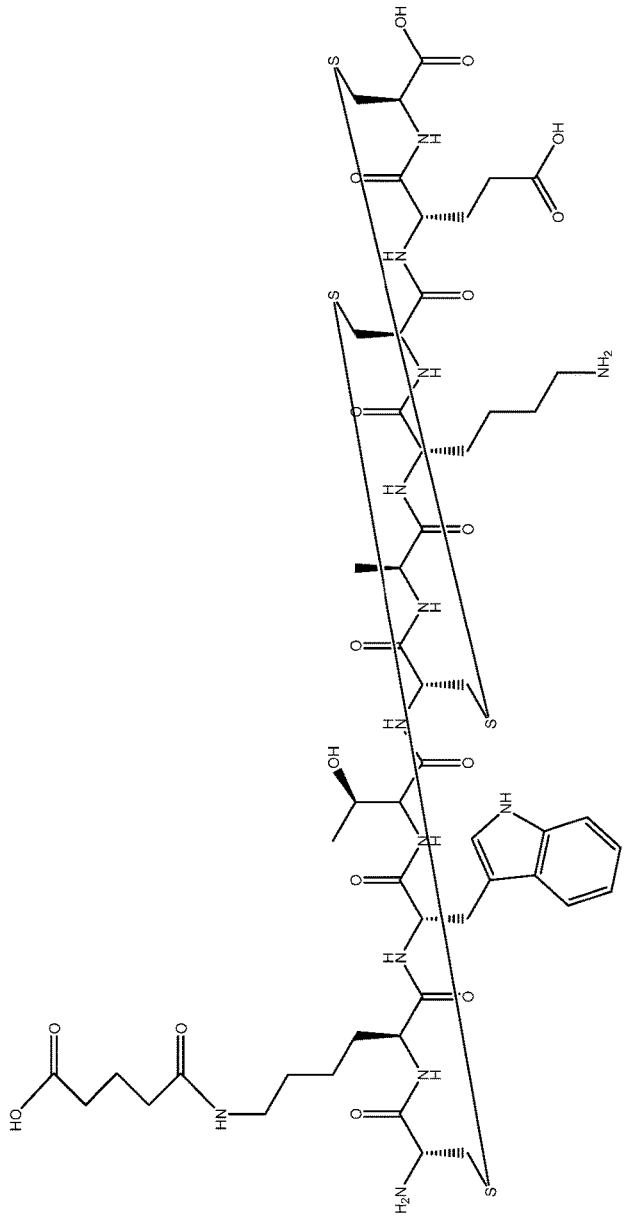
Figure 26A:
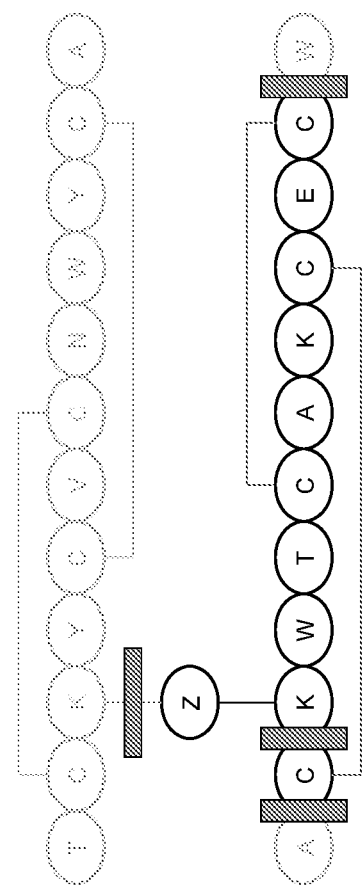
Figure 26B:
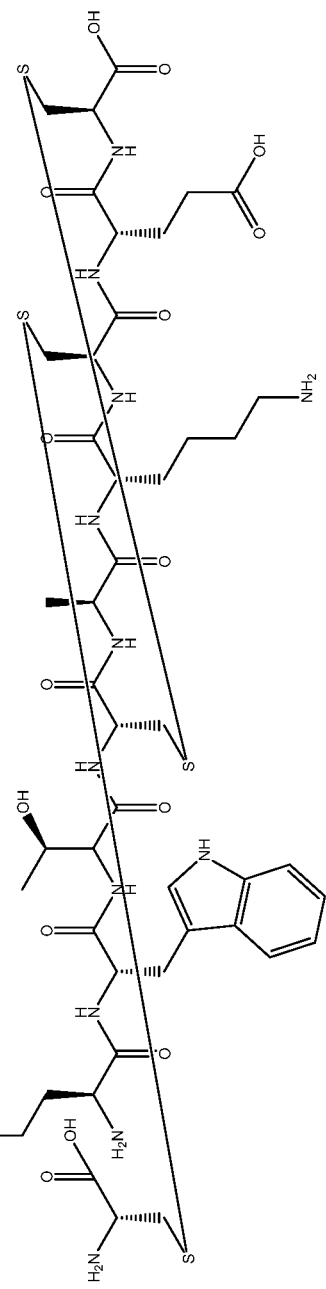

FIG. 16 shows a flow diagram of a searching process in accordance with one embodiment of the invention, which may be performed asynchronously with the first phase of operation of the invention. The process utilizes the database or databases of stored induced connected subgraph records created in the first phase of operation. At step 1605, the system receives a query molecular weight. At steps 1610 and 1620, the system searches the databases of stored induced connected subgraph records generated at Steps 630 and 635 using the query molecular weight in order to identify induced connected subgraph records having molecular weight field values that match the query molecular weight, i.e., records that have molecular weights in the molecular weight field that are within a specified range of the query molecular weight, preferably within ±5 ppm of the query molecular mass, more preferably with ±4 ppm of the query molecular mass, and more preferably within +2 ppm of the query molecular mass. In some embodiments, the search of the induced connected subgraph records may be carried out by a search engine module (i.e., a computer program) comprising program instructions that, when executed by the microprocessor 425, will cause the microprocessor 425 to search for and retrieve data from the ICS records stored in the subgraph database during an earlier-executed phase of operation of the invention in which the ICS records for the component parts of the chosen molecule are generated and stored in the subgraph database 490. The query molecular weight is typically an experimentally observed or known molecular weight of a substructure of the chosen molecule.

A query molecular weight may be generated using technology such as mass spectrometry, and particularly differential mass spectrometry.

At steps 1615 and 1625, the system stores vertex values from the vertex data field and edge values from the edge data field for the identified induced connected subgraph record in the subgraph database. The system may, optionally, display to this information to the user. The display step is achieved by transmitting the vertex values and edge values from the identified ICS record to a user interface for presentation on a display device operated by an end user.

In an additional embodiment of the invention, the system may use the vertex values in the vertex data field, the edge values in the edge data field and the chosen molecule data to produce and store in the memory of the computer system a graphical representation of an induced connected subgraph of the line graph, and transmit the graphical representation from the memory of the computer system to the display device operated by the end user. See Step 1660 of FIG. 16. The graphical representation may be an MCU graph or a chemical structure diagram of the substructure represented by the induced connected subgraph record. It is noted that displaying the graphical representation, as set forth at Step 1660, is an optional step, depending on whether the user wishes to see the graphical representation, or is satisfied with receiving (or being presented with) the vertex values and the edge values for the induced connected subgraphs of the line graph.

At step 1630, the system calculates an adjusted query molecular weight by subtracting the molecular weight of the cut vertex from the query molecular weight. At step 1635, the system searches the first ICS database, which contains ICS records of a first component of the chosen molecule, to identify the ICS record with the lowest molecular weight in the molecular weight field. The system then, at step 1640, calculates a modified query molecular weight by subtracting the lowest molecular weight in the molecular weight field of the ICS records of the first database from the adjusted query molecular weight.

At step 1645, the system performs a binary search of the second database, which contains ICS records of the second component of the chosen molecule, to identify an ICS with a molecular weight that, when combined with the molecular weight of the ICS record identified from the search of the first database, matches the modified query molecular weight. As set forth in step 1650, if the combined molecular weight of the ICS records from the first and second databases match the modified query molecular weight, then the system moves on to step 1655 and transmits the vertex values in the vertex field and the edge values in the edge field from the identified ICS records to the user interface for presentation on a display device operated by an end user.

In an additional embodiment of the invention, the system may use the vertex values in the vertex data field, the edge values in the edge data field and the chosen molecule data to produce a graphical representation of an induced connected subgraph of the line graph and transmit the graphical representation to the display device operated by the end user. See Step 1660 of FIG. 16. The graphical representation may be an MCU graph or a chemical structure diagram of the substructure represented by the induced connected subgraph record. It is noted that displaying the graphical representation, as set forth at Step 1660, is an optional step, depending on whether the user wishes to see the graphical representation, or is satisfied with receiving (or being presented with) the vertex values and the edge values for the induced connected subgraphs of the line graph.

At step 1665, the system searches the first database to determine if there is another ICS record located therein and if so, repeats step 1635 to identify the ICS record having the next lowest molecular weight. This lowest molecular weight is then subtracted from the adjusted query molecular weight to provide a new modified query molecular weight that is then used to in a binary search of the second database. Steps 1635-1665 are repeated until the molecular weights of all ICS records in the first database have been utilized in binary searches of the second database.

FIG. 17A-17D are exemplary database records of monomer A generated in accordance with an embodiment of the invention. FIGS. 18A-18D are exemplary database records of monomer B generated in accordance with an embodiment of the present invention.

FIGS. 19A, 19B, 20A, 20B, 21A, 21B, 22A and 22B show MCU graphs and chemical structures of substructures of monomer A, generated in accordance with an embodiment of the invention, and corresponding to the database entries depicted in FIGS. 17A-17D, respectively. In embodiments of the present invention, the visualizer produces graphical representations of the these substructures and send them to the second user's display device.

FIGS. 23A, 23B, 24A, 24B, 25A, 25B, 26A and 26B show MCU graphs and chemical structures of substructures of monomer B, generated in accordance with an embodiment of the invention, and corresponding to the database entries depicted in FIGS. 18A-18D, respectively.

Figure 27A:
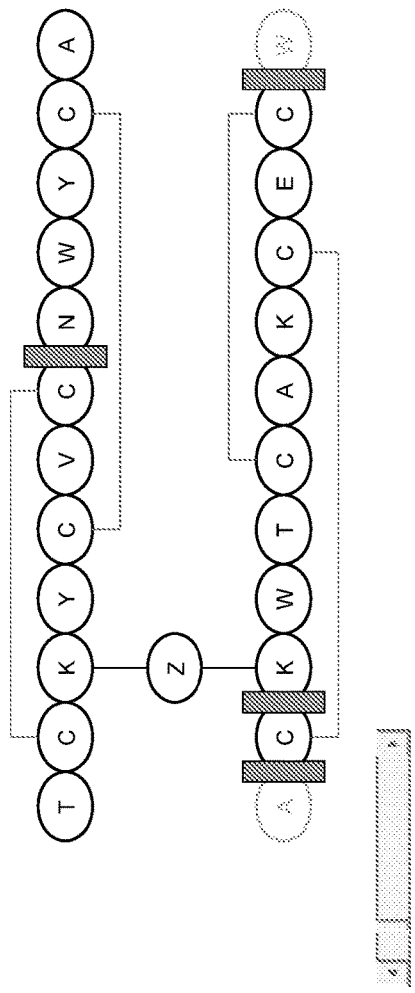
FIGS. 27A and 27B show an MCU graph and chemical structure of a substructure of monomer A combined with a substructure of monomer B, generated in accordance with an embodiment of the invention.
Figure 27B:
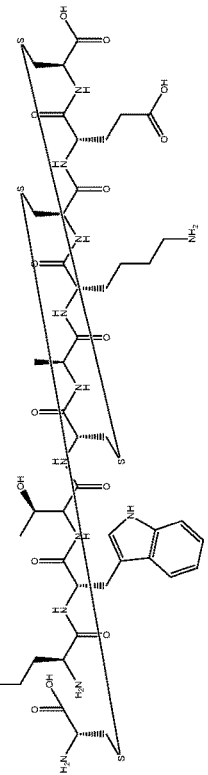

FIGS. 27A and 27B show, respectively, a chemical diagram and an MCU graph for a combination of a substructure of monomer A combined with a substructure of monomer B of the chosen molecule generated in accordance with an embodiment of the invention.

FIG. 28 shows exemplary MatLab code program instructions for populating a substructure database from MCU graph data stored in an MCU graph adjacency matrix. As shown in FIG. 28, the functions in the code receive as input data stored in an MCU graph adjacency matrix data structure E2V and the data stored in a line graph adjacency matrix data structure J. Note that the latter may be derived from the former. Therefore, the algorithm represented by the MatLab code shown in FIG. 28 may be written so that it ONLY requires the data from the MCU graph adjacency matrix data structure to populate the ICS database.

Figure 29:
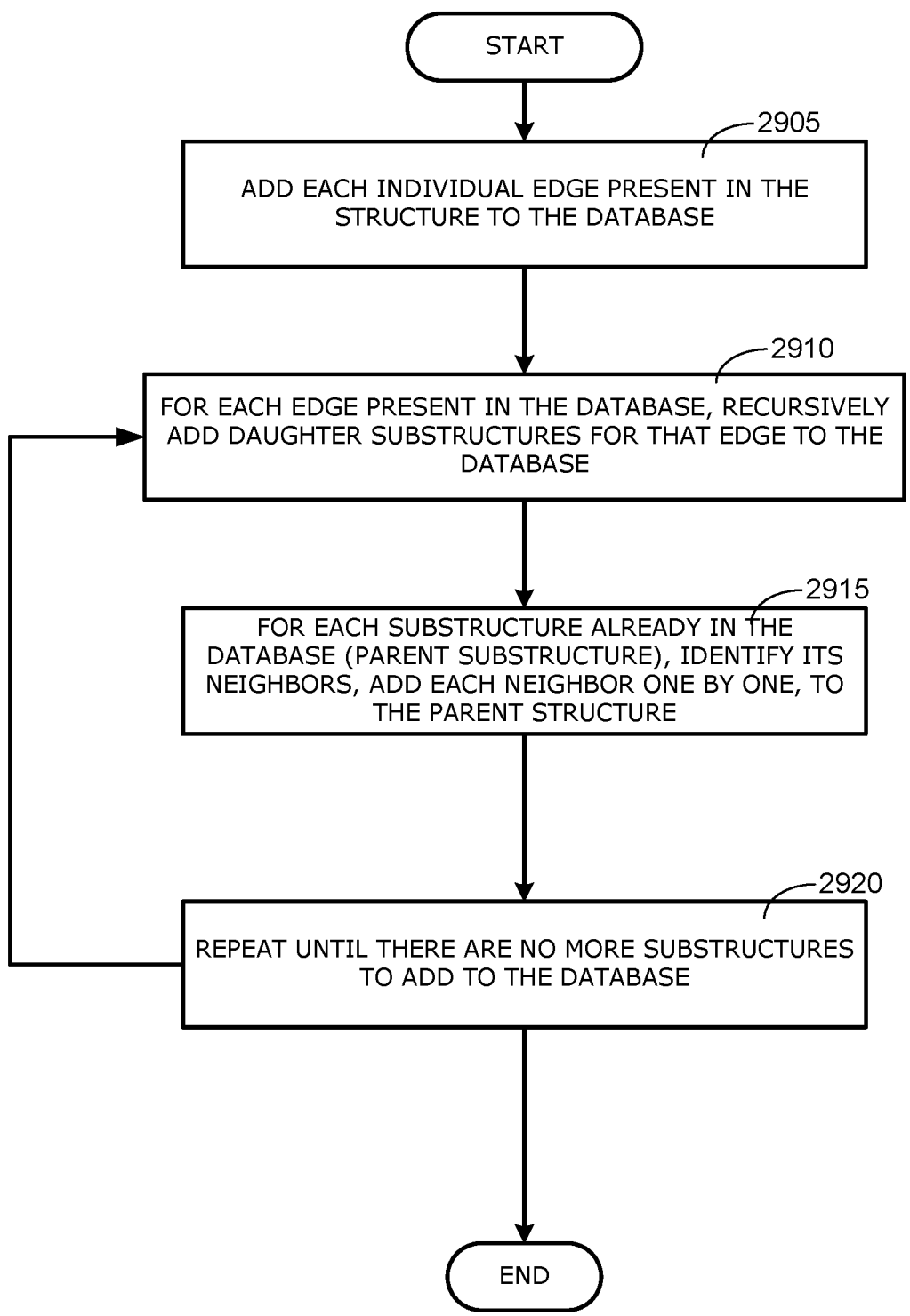
FIG. 29 shows a flow diagram illustrating the algorithm performed by the exemplary program instructions shown in FIG. 28.

FIG. 29 shows a flow diagram illustrating the algorithm performed by the exemplary code shown in FIG. 28. As shown in FIG. 29, the algorithm for traversing the graph data structure to populate the subgraph database comprises the following steps: First, at step 2905, add to the database data representing each individual edge present in the structure. Then, at step 2910, for each edge present in the database, recursively add to the database all of the daughter substructures for that edge. Next, at step 2915, for each substructure already in the database (i.e., each parent substructure), identify its neighbors and add each neighbor, one by one, to the parent structure and, at step 2920, repeat steps 2910, 2915 and 2920 until there are no more substructures to add to the database.

While the invention has been described in detail with reference to specific examples, it will be apparent to one skilled in the art that various modifications can be made within the scope of this invention. Thus, the scope of the invention should not be limited by the examples described herein, but by the claims presented below.

We claim:

1. A system for identifying substructures of a chosen molecule, the system comprising:
   a) a microprocessor;
   b) a memory;
   c) an application program, in the memory, comprising program instructions that, when executed by the microprocessor, will cause the microprocessor to
      (i) receive and store in the memory chosen molecule data representing (A) a set of minimum cleavable units (MCUs) in the chosen molecule, (B) a set of bonds connecting the set of MCUs in the chosen molecule, (C) molecular weights for each MCU, (D) a connectivity profile for the chosen molecule, the connectivity profile indicating relative positions of MCUs and bonds and connections therebetween, and (E) a cut vertex in the chosen molecule, wherein removal of the cut vertex separates the molecule into a first component and a second component,
      (ii) based on the chosen molecule data, create and store in the memory a first MCU graph data structure for the first component of the chosen molecule, the first MCU graph data structure being populated with first MCU graph data representing a first MCU graph for the first component, the first MCU graph having a plurality of first MCU graph vertices and a plurality of first MCU graph edges, each first MCU graph vertex corresponding to a MCU of the first component and each first MCU graph edge corresponding to a first bond connecting MCUs in the first component,
      (iii) based on the first MCU graph data, generate and store in the memory a first line graph ("LG") data structure for the first component of the chosen molecule, the first LG data structure being populated with first LG data representing a first LG for the first MCU graph, the first LG having a plurality of first LG vertices and a plurality of first LG edges, each first LG vertex corresponding to a first MCU graph edge in the first MCU graph and each first LG edge corresponding to a pair of first MCU graph vertices in the first MCU graph that are connected together by said first MCU graph edge,
      (iv) execute a graph traversal algorithm against the first LG data in the first LG data structure for the first component of the chosen molecule to determine a plurality of first induced connected subgraphs ("ICSs") for the first LG, each first ICS comprising a first connected subset of first LG vertices and first LG edges in the first LG, and a first physical arrangement of said first connected subset of first LG vertices and first LG edges, that together uniquely corresponds to a first connected subset of the set of MCUs and bonds, and the relative positions of said first connected subset of MCUs and bonds in the chosen molecule,
      (v) for each first ICS represented in the first LG data structure for the first component of the chosen molecule, create and store in a database a first ICS record comprising a first molecular weight field, a first vertex data field and a first edge data field, wherein the first vertex data field is populated with first vertex values configured to indicate a first vertex position for every first LG vertex in the first ICS, and the first edge data field is populated with first edge values configured to indicate the first edge position of every first LG edge in the first ICS relative to the first LG vertices, (vi) for each first ICS record in the first LG data structure for the first component of the chosen molecule, calculate and store in the first molecular weight field a first total molecular weight for the first ICS of that first ICS record based on the chosen molecule data for the chosen molecule and the first vertex values and the first edge values in the first ICS record, (vii) based on the chosen molecule data, create and store in the memory a second MCU graph data structure for the second component of the chosen molecule, the second MCU graph data structure being populated with second MCU graph data representing a second MCU graph for the second component, the second MCU graph having a plurality of second MCU graph vertices and a plurality of second MCU graph edges, each second MCU graph vertex corresponding to a MCU of the second component and each second MCU graph edge corresponding to a second bond connecting MCUs in the second component, (viii) based on the second MCU graph data, generate and store in the memory a second LG data structure for the second component of the chosen molecule, the second LG data structure being populated with second LG data representing a second LG for the second MCU graph, the second LG having a plurality of second LG vertices and a plurality of second LG edges, each second LG vertex corresponding to a second MCU graph edge in the second MCU graph and each second LG edge corresponding to a pair of second MCU graph vertices in the second MCU graph that are connected together by said second MCU graph edge, (ix) execute the graph traversal algorithm against the second LG data in the second LG data structure for the second component of the chosen molecule to determine a plurality of second ICSs for the second LG, each second ICS comprising a second connected subset of second LG vertices and second LG edges in the second LG, and a second physical arrangement of said second connected subset of second LG vertices and second LG edges, that together uniquely corresponds to a second connected subset of the set of MCUs and bonds, and the relative positions of said second connected subset of MCUs and bonds in the chosen molecule, (x) for each second ICS represented in the second LG data structure for the second component of the chosen molecule, create and store in the database a second ICS record comprising a second molecular weight field, a second vertex data field and a second edge data field, wherein the second vertex data field is populated with second vertex values configured to indicate a second vertex position for every second LG vertex in the second ICS, and the second edge data field is populated with second edge values configured to indicate the second edge position of every second LG edge in the second ICS relative to the second LG vertices, and (xi) for each second ICS record in the second LG data structure for the second component of the chosen molecule, calculate and store in the second molecular weight field a second total molecular weight for the second ICS of that second ICS record based on the chosen molecule data for the chosen molecule and the second vertex values and the second edge values in the second ICS record; and d) a user interface comprising program instructions that, when executed by the microprocessor, will cause the microprocessor to (i) receive a query molecular weight from an end user, (ii) search the database to identify a first ICS record having a first total molecular weight in the first molecular weight field that matches the query molecular weight, (iii) search the database to identify a second ICS record having a second total molecular weight in the second molecular weight field that matches the query molecular weight, (iv) use the first vertex values in the first vertex data field and the first edge values in the first edge data field of the identified first ICS records to produce and display on a display device a first graphical representation of the first ICS corresponding to the first ICS record having the first total molecular weight that matches the query molecular weight, (v) use the second vertex values in the second vertex data field and the second edge values in the second edge data field of the identified second ICS records to generate and display on the display device a second graphical representation of the second ICS corresponding to the second ICS record having the second total molecular weight that matches the query molecular weight, (vi) calculate an adjusted query molecular weight by subtracting a molecular weight for the cut vertex from the query molecular weight, (vii) identify, for the first component of the chosen molecule, a first partial ICS record, the first partial ICS record having the lowest first molecular weight in the first molecular weight field relative to all the other molecular weights in the all the other molecular weight fields for the first component, (viii) calculate a modified query molecular weight by subtracting the lowest first molecular weight of the first partial ICS record for the first component of the chosen molecule from the adjusted query molecular weight, (ix) use the modified query molecular weight to search the ICS records for the second component of the chosen molecule to identify a second partial ICS record for the second component of the chosen molecule, the second partial ICS record having a second molecular weight in the second molecular weight field that, when combined with the first molecular weight of the first partial ICS record for the first component, matches the modified query molecular weight, (x) use the vertex values in the vertex data fields for the first and second partial ICS records, the edge values in the edge data fields for the first and second partial ICS records, the cut vertex and the chosen molecule data to generate and display on the display device a graphical representation of a combined ICS for the first and second components of the chosen molecule, wherein the combined ICS is produced by concatenating together an ICS for the first partial ICS record and an ICS for the second partial ICS record, (xi) replace the first partial ICS record with another first ICS record, wherein said another first ICS record comprises the next lowest first molecular weight in the first molecular weight field relative to molecular weight in the molecular weight field of the first partial ICS record, and (xii) repeat steps viii) through xi) above until each of the first molecular weights in the first molecular weight fields of the first ICS records for the first component of the chosen molecule have been used to carry out the steps viii) though xi).

2. The system of claim 1, further comprising program instructions in the application program that, when executed by the microprocessor, causes the microprocessor to
 a) receive a specified tolerance for the query molecular weight;
 b) use the specified tolerance to calculate and define a range of query molecular weights for the search of the database;
 c) search the database based on the query molecular weight and the range to identify each ICS record in the database that has a total molecular weight in the molecular weight field that falls within the defined range of molecular weights, and
 d) for said each identified ICS record, transmit the vertex values in the vertex data field and the edge values in the edge data field to the user interface for presentation to the end user.

3. The system according to claim 1, wherein the chosen molecule data is received by parsing information stored in a linked list, or an array, or an adjacency matrix, or a graphic image file, or a chemical drawing file, or a spreadsheet file, or a text file, or a CSV file, or a .CDX file, or a .CDXML file, or a .MOL file, or a .SDM file, or a CAD file, or a binary data file.

4. The system according to claim 1, wherein at least one of the first connected subset of the set of MCUs and bonds and the second connected subset of the set of MCUs and bonds is a metabolite of the chosen molecule, or a catabolite of the chose molecule, or a gas phase fragmentation of the chosen molecule, or a degradant of the chosen molecule, or a substructure of the chosen molecule.

5. The system according to claim 1, wherein the first MCU graph data structure or the second MCU graph data structure is an array, an adjacency matrix, an adjacency list, an incidence matrix or an incidence list.

6. The system according to claim 1, wherein the first LG data structure or the second LG data structure is an array, an adjacency matrix, an adjacency list, an incidence matrix, or an incidence list.

7. The system according to claim 1, wherein the graph traversal algorithm is a depth-first search algorithm, or a breadth-first search algorithm, or a reverse-search algorithm, or a tree-search algorithm, or a combination of two of more of the graph traversal algorithms recited herein.

8. The system according to claim 1, wherein:
 a) the chosen molecule data includes elemental composition data representing (A) a set of elemental units in each MCU, (B) a set of elemental bonds connecting the set of elemental units in the MCU, (C) elemental molecular weights for each elemental unit, and (D) an MCU connectivity profile for the MCU, the MCU connectivity profile indicating relative positions of elemental units and elemental bonds in the MCUs and connections therebetween;
 b) the first ICS record or the second ICS record created in the database further comprises an elemental unit field populated with one or more elemental unit identifiers; and c) the application program further includes program instructions that, when executed by the microprocessor, will cause the microprocessor to
  (i) receive a query elemental unit from the end user,
  (ii) search the database based on the query elemental unit to identify an ICS record having an elemental unit identifier in the elemental unit field that matches the query elemental unit, and
  (iii) transmit the vertex values in the vertex data field and the edge values in the edge data field for the identified ICS record to the user interface for presentation on a display device operated by the end user.

9. The system according to claim 1, wherein:
 a) each ICS record created in the database further comprises a biotransformation count field; and
 b) the user interface further includes program instructions that, when executed by the microprocessor, will cause the microprocessor to
  i) receive a maximum biotransformation count from the end user, and
  ii) search the database based on the query mass and the maximum biotransformation count to identify an ICS record having a molecular weight value in the molecular weight field that matches the query mass and a biotransformation count value in the biotransformation count field that does not exceed the biotransformation count maximum.

10. The system according to claim 1, wherein:
 a) each ICS record created in the database further comprises a biotransformation count field; and
 b) the user interface further includes program instructions that, when executed by the microprocessor, will cause the microprocessor to
  i) determine a rank order between the first ICS, the second ICS and the combined ICS, based on the biotransformation count field of said each ICS record, and
  ii) display the first graphical representation of the first ICS, the second graphical representation of the second ICS and the graphical representation of the combined ICS on the display device in accordance with the rank order.

11. A system for generating a database to facilitate identifying substructures of a chosen molecule using a microprocessor, the system comprising:
 a) a memory;
 b) a microprocessor;
 c) an input module for receiving and storing chosen molecule data representing (A) a set of MCUs in the chosen molecule, (B) a set of bonds connecting the set of MCUs in the chosen molecule, (C) molecular weights for each MCU, (D) a cut vertex located within the chosen molecule, that when removed, separates the chosen molecule into a first component and a second component, and (E) a connectivity profile for the MCUs and the bonds in the chosen molecule, the connectivity profile indicating relative positions of MCUs and bonds and connections therebetween;
 d) an MCU graph data structure generator configured to create and store in the memory i) a first MCU graph data structure for the first component of the chosen molecule, the first MCU graph data structure being populated with first MCU graph data representing a first MCU graph for the first component, the first MCU graph having a plurality of first MCU graph vertices and a plurality of first MCU graph edges, each first MCU graph vertex corresponding to a MCU of the first component and each first MCU graph edge corresponding to a first bond connecting MCUs in the first component and ii) a second MCU graph data structure for the second component of the chosen molecule, the second MCU graph data structure being populated with second MCU graph data representing a second MCU graph for the second component, the second MCU graph having a plurality of second MCU graph vertices and a plurality of second MCU graph edges, each second MCU graph vertex corresponding to a MCU of the second component and each second MCU graph edge corresponding to a second bond connecting MCUs in the second component;

e) a LG data structure generator configured to i), based on the first MCU graph data, generate and store in the memory a first LG data structure for the first component of the chosen molecule, the first LG data structure being populated with first LG data representing a first LG for the first MCU graph, the first LG having a plurality of first LG vertices and a plurality of first LG edges, each first LG vertex corresponding to a first MCU graph edge in the first MCU graph and each first LG edge corresponding to a pair of first MCU graph vertices in the first MCU graph that are connected together by said first MCU graph edge; and ii) based on the second MCU graph data, generate and store in the memory a second LG data structure for the second component of the chosen molecule, the second LG data structure being populated with second LG data representing a second LG for the second MCU graph, the second LG having a plurality of second LG vertices and a plurality of second LG edges, each second LG vertex corresponding to a second MCU graph edge in the second MCU graph and each second LG edge corresponding to a pair of second MCU graph vertices in the second MCU graph that are connected together by said second MCU graph edge;

f) a graph traversing module configured to i) execute a graph traversal algorithm against the first LG data in the first LG data structure for the first component of the chosen molecule to determine a plurality of first ICSs for the first LG, each first ICS comprising a first connected subset of first LG vertices and first LG edges in the first LG, and a first physical arrangement of said first connected subset of first LG vertices and first LG edges, that together uniquely corresponds to a first connected subset of the set of MCUs and bonds, and the relative positions of said first connected subset of MCUs and bonds in the chosen molecule, and ii) execute the graph traversal algorithm against the second LG data in the second LG data structure for the second component of the chosen molecule to determine a plurality of second ICSs for the second LG, each second ICS comprising a second connected subset of second LG vertices and second LG edges in the second LG, and a second physical arrangement of said second connected subset of second LG vertices and second LG edges, that together uniquely corresponds to a second connected subset of the set of MCUs and bonds, and the relative positions of said second connected subset of MCUs and bonds in the chosen molecule; and g) a subgraph database generator that
(i) for each first ICS represented in the first LG data structure for the first component of the chosen molecule, creates in a subgraph database a first ICS record comprising a first molecular weight field, a first vertex data field and a first edge data field, wherein the first vertex data field is populated with first vertex values configured to indicate a first vertex position for every first LG vertex in the first ICS, and the first edge data field is populated with first edge values configured to indicate the first edge position of every first LG edge in the first ICS relative to the first LG vertices, and
(ii) for each second ICS represented in the second LG data structure for the second component of the chosen molecule, create in the subgraph database a second ICS record comprising a second molecular weight field, a second vertex data field and a second edge data field, wherein the second vertex data field is populated with second vertex values configured to indicate a second vertex position for every second LG vertex in the second ICS, and the second edge data field is populated with second edge values configured to indicate the second edge position of every second LG edge in the second ICS relative to the second LG vertices; and h) a molecular weight calculator that i) for each first ICS record in the first LG data structure for the first component of the chosen molecule, calculates and stores in the first molecular weight field a first total molecular weight for the first ICS of that first ICS record based on the chosen molecule data for the chosen molecule and the first vertex values and the first edge values in the first ICS record; and ii) for each second ICS record in the second LG data structure for the second component of the chosen molecule, calculates and stores in the second molecular weight field a second total molecular weight for the second ICS of that second ICS record based on the chosen molecule data for the chosen molecule and the second vertex values and the second edge values in the second ICS record.

12. The system of claim 11, wherein the chosen molecule data is received by parsing information stored in a linked list, or an array, or an adjacency matrix, or a graphic image file, or a chemical drawing file, or a spreadsheet file, or a text file, or a CSV file, or a .CDX file, or a .CDXML file, or a .MOL file, or a .SDM file, or a CAD file, or a binary data file.

13. The system according to claim 11, wherein at least one of the first connected subset of the set of MCUs and bonds and the second connected subset of the set of MCUs and bonds is a metabolite of the chosen molecule, or a catabolite of the chose molecule, or a gas phase fragmentation of the chosen molecule, or a degradant of the chosen molecule, or a substructure of the chosen molecule.

14. The system according to claim 11, wherein the first MCU graph data structure or the second MCU graph data structure is an array, an adjacency matrix, an adjacency list, an incidence matrix or an incidence list.

15. The system according to claim 11, wherein the first LG data structure or the second LG data structure is an array, an adjacency matrix, an adjacency list, an incidence matrix, or an incidence list.

16. The system according to claim 11, wherein the graph traversal algorithm is a depth-first search algorithm, or a breadth-first search algorithm, or a reverse-search algorithm, or a tree-search algorithm, or a combination of two of more of the graph traversal algorithms recited herein.

17. The system according to claim 11, further comprising:
a) a user interface for communication with an end user; and b) a search engine in the memory having program instructions that, when executed by the microprocessor, will cause the microprocessor to
  i) receive a query molecular weight from the end user,
  ii) search the database based on the query molecular weight to identify an ICS record having a total molecular weight in the molecular weight field that matches the query molecular weight, and
  iii) transmit the vertex values in the vertex data field and the edge values in the edge data field for the identified ICS record to the user interface for presentation on a display device operated by the end user,
  iv) calculate an adjusted query molecular weight by subtracting the molecular weight of the cut vertex from the query molecular weight,
  v) identify the ICS record, for the first component of the chosen molecule, having the lowest molecular weight,
  vi) calculate a modified query molecular weight by subtracting the lowest molecular weight of the ICS record for the first component of the chosen molecule from the adjusted query molecular weight,
  vii) using the modified query molecular weight, perform a binary search of the ICS records for the second component of the chosen molecule to identify an ICS record that, when combined with the molecular weight of the ICS record for the first component, matches the modified query molecular weight,
  viii) transmit the vertex values in the vertex data field and the edge values in the edge data field for the identified ICS record to the user interface for presentation on a display device operated by the end user,
  ix) identify the ICS record for the first component of the chosen molecule that has the next lowest molecular weight, and
  x) repeat steps vi) through ix) until each of the molecular weights for the ICS records for the first component of the chosen molecule have been used in steps vi) through viii).

18. The system according to claim 17, further comprising program instructions in the user interface that, when executed by the microprocessor, will cause the microprocessor to:
  a) use the vertex values in the vertex data field, the edge values in the edge data field and the chosen molecule data to produce a graphical representation of ICS of the LG for the first component and the second component of the chosen molecule; and
  b) transmit the graphical representation to the display device operated by the end user.

19. The system of claim 18, further comprising program instructions in the user interface that, when executed by the microprocessor, causes the microprocessor to
  a) receive a specified tolerance for the molecular weight;
  b) use the specified tolerance to calculate and define a range of molecular weights for the search of the database;
  c) search the database based on the query molecular weight and the range to identify each ICS record in the database that has a total molecular weight in the molecular weight field that falls within the defined range of molecular weights, and
  d) for said each identified ICS record, transmit the vertex values in the vertex data field and the edge values in the edge data field to the user interface for presentation to the end user;
  e) calculate an adjusted query molecular weight by subtracting the molecular weight of the cut vertex from the query molecular weight;
  f) identify the ICS record, for the first component of the chosen molecule, having the lowest molecular weight;
  g) calculate a modified query molecular weight by subtracting the lowest molecular weight of the ICS record for the first component of the chosen molecule from the adjusted query molecular weight;
  h) using the modified query molecular weight, perform a binary search of the ICS records for the second component of the chosen molecule to identify an ICS record that, when combined with the molecular weight of the ICS record for the first component, matches the modified query molecular weight;
  i) transmit the vertex values in the vertex data field and the edge values in the edge data field for the identified ICS record to the user interface for presentation on a display device operated by the end user;
  j) identify the ICS record for the first component of the chosen molecule that has the next lowest molecular weight; and
  k) repeat steps f) through j) until each of the molecular weights for the ICS records for the first component of the chosen molecule have been used in steps g) through j).

20. The system according to claim 11, wherein the graph traversal algorithm is a depth-first search, breadth-first search, a reverse-search, a tree-search, or a combination of two of more of the graph traversal algorithms recited herein.

21. The system according to claim 11, wherein the chosen molecule is a protein, nucleic acid, oligonucleotide, polynucleotide, polysaccharide or synthetic polymer.

22. A method for generating a database of substructures for a chosen molecule using a microprocessor and a memory device, the method comprising:
  a) receiving and storing in the memory chosen molecule data representing (A) a set of MCUs in the chosen molecule, (B) a set of bonds connecting the set of MCUs in the chosen molecule, (C) molecular weights for each MCU, (D) a connectivity profile for the chosen molecule, the connectivity profile indicating relative positions of MCUs and bonds and connections therebetween, and (E) a cut vertex in the chosen molecule, wherein removal of the cut vertex separates the molecule into a first component and a second component;
  b) based on the chosen molecule data, creating and storing in the memory a first MCU graph data structure for the first component of the chosen molecule, the first MCU graph data structure being populated with first MCU graph data representing a first MCU graph for the first component, the first MCU graph having a plurality of first MCU graph vertices and a plurality of first MCU graph edges, each first MCU graph vertex corresponding to a MCU of the first component and each first MCU graph edge corresponding to a first bond connecting MCUs in the first component;
  c) based on the first MCU graph data, generating and storing in the memory a first LG data structure for the first component of the chosen molecule, the first LG data structure being populated with first LG data representing a first LG for the first MCU graph, the first LG having a plurality of first LG vertices and a plurality of first LG edges, each first LG vertex corresponding to a first MCU graph edge in the first MCU graph and each first LG edge corresponding to a pair of first MCU graph vertices in the first MCU graph that are connected together by said first MCU graph edge;

d) executing a graph traversal algorithm against the first LG data in the first LG data structure for the first component of the chosen molecule to determine a plurality of first ICSs for the first LG, each first MCS comprising a first connected subset of first LG vertices and first LG edges in the first LG, and a first physical arrangement of said first connected subset of first LG vertices and first LG edges, that together uniquely corresponds to a first connected subset of the set of MCUs and bonds, and the relative positions of said first connected subset of MCUs and bonds in the chosen molecule;

e) for each first ICS represented in the first LG data structure for the first component of the chosen molecule, creating in a database a first ICS record comprising a first molecular weight field, a first vertex data field and a first edge data field, wherein the first vertex data field is populated with first vertex values configured to indicate a first vertex position for every first LG vertex in the first ICS, and the first edge data field is populated with first edge values configured to indicate the first edge position of every first LG edge in the first ICS relative to the first LG vertices;

f) for each first ICS record in the first LG data structure for the first component of the chosen molecule, calculating and storing in the first molecular weight field a first total molecular weight for the first ICS of that first ICS record based on the chosen molecule data for the chosen molecule and the first vertex values and the first edge values in the first ICS record;

g) based on the chosen molecule data, creating and storing in the memory a second MCU graph data structure for the second component of the chosen molecule, the second MCU graph data structure being populated with second MCU graph data representing a second MCU graph for the second component, the second MCU graph having a plurality of second MCU graph vertices and a plurality of second MCU graph edges, each second MCU graph vertex corresponding to a MCU of the second component and each second MCU graph edge corresponding to a second bond connecting MCUs in the second component;

h) based on the second MCU graph data, generating and storing in the memory a second LG data structure for the second component of the chosen molecule, the second LG data structure being populated with second LG data representing a second LG for the second MCU graph, the second LG having a plurality of second LG vertices and a plurality of second LG edges, each second LG vertex corresponding to a second MCU graph edge in the second MCU graph and each second LG edge corresponding to a pair of second MCU graph vertices in the second MCU graph that are connected together by said second MCU graph edge;

i) executing the graph traversal algorithm against the second LG data in the second LG data structure for the second component of the chosen molecule to determine a plurality of second ICSs for the second LG, each second ICS comprising a second connected subset of second LG vertices and second LG edges in the second LG, and a second physical arrangement of said second connected subset of second LG vertices and second LG edges, that together uniquely corresponds to a second connected subset of the set of MCUs and bonds, and the relative positions of said second connected subset of MCUs and bonds in the chosen molecule;

j) for each second ICS represented in the second LG data structure for the second component of the chosen molecule, creating in a database a second ICS record comprising a second molecular weight field, a second vertex data field and a second edge data field, wherein the second vertex data field is populated with second vertex values configured to indicate a second vertex position for every second LG vertex in the second ICS, and the second edge data field is populated with second edge values configured to indicate the second edge position of every second LG edge in the second ICS relative to the second LG vertices; and k) for each second ICS record in the second LG data structure for the second component of the chosen molecule, calculating and storing in the second molecular weight field a second total molecular weight for the second ICS of that second ICS record based on the chosen molecule data for the chosen molecule and the second vertex values and the second edge values in the second ICS record.

23. The method according to claim 22, wherein the graph traversal algorithm is a depth-first search, or a breadth-first search, or a reverse-search, or a tree-search, or a combination of two of more of the graph traversal algorithms recited herein.

24. The method according to claim 22, further comprising:

a) receiving a query molecular weight by the microprocessor;

b) with the microprocessor, searching the database based on the query molecular weight to identify an ICS record having in the molecular weight field a total molecular weight that matches the query molecular weight;

c) transmitting a representation of the vertex values in the vertex data field and the edge values in the edge data field for the identified ICS record to a display device;

d) calculate an adjusted query molecular weight by subtracting the molecular weight of the cut vertex from the query molecular weight;

e) identify the ICS record, for the first component of the chosen molecule, having the lowest molecular weight;

f) calculate a modified query molecular weight by subtracting the lowest molecular weight of the ICS record for the first component of the chosen molecule from the adjusted query molecular weight;

g) using the modified query molecular weight, perform a binary search of the ICS records for the second component of the chosen molecule to identify an ICS record that, when combined with the molecular weight of the ICS record for the first component, matches the modified query molecular weight;

h) transmit the vertex values in the vertex data field and the edge values in the edge data field for the identified ICS record to a user interface for presentation on a display device operated by an end user; and i) identify the ICS record for the first component of the chosen molecule that has the next lowest molecular weight; and repeat steps f) through h) until each of the molecular weights for the ICS records for the first component of the chosen molecule have been used in steps f) through h).

25. The method according to claim 22, further comprising:
a) with the microprocessor, producing a graphical representation of an ICS of the LG for the first component and second component of the chosen molecule based on the connectivity profile of the chosen molecule, the vertex values in the vertex data field and the edge values in the edge data field; and
b) transmitting the graphical representation to the display device.

26. The method according to claim 22, wherein the chosen molecule is a small molecule.

27. The method according to claim 22, wherein the chosen molecule is a macromolecule.

28. The method according to claim 27, wherein the macromolecule is a protein, nucleic acid, oligonucleotide, polynucleotide, polysaccharide or synthetic polymer.

29. The method according to claim 22, wherein at least one of the first connected subset of the set of MCUs and bonds and the second connected subset of the set of MCUs and bonds is a metabolite of the chosen molecule, or a catabolite of the chose molecule, or a gas phase fragmentation of the chosen molecule, or a degradant of the chosen molecule, or a substructure of the chosen molecule.

30. An apparatus for searching a database to find and transmit to a display device information describing a set of component parts for a chemical substructure of a chosen molecule and a physical arrangement of said component parts using a microprocessor, the apparatus comprising:
a) an electronic user interface to a database comprising a multiplicity of ICS records, each ICS record comprising a molecular weight field, a vertex data field and an edge data field, wherein the vertex data field is populated with vertex values configured to indicate a vertex position for every vertex in an ICS for a LG representing a connectivity profile of the chosen molecule, and the edge data field is populated with edge values configured to indicate an edge position for every edge in the ICS;
b) an input module, operable with the electronic user interface, configured to receive a specified molecular weight from an end user;
c) a search engine having program instructions that, when executed by the microprocessor, will cause the microprocessor to find in the database at least one ICS record in which the total molecular weight in the molecular weight field is equivalent to the specified molecular weight; and
d) a visualizer, stored in the memory, configured to transmit the vertex values of the vertex data field and the edge values of the edge data field for said at least one ICS record to the display device.

* * * * *